US010058533B2

(12) United States Patent
Sun

(10) Patent No.: US 10,058,533 B2
(45) Date of Patent: Aug. 28, 2018

(54) PHARMACEUTICAL COMPOSITION CONTAINING GINKGOLIDE B AND XA FACTOR INHIBITOR, PREPARATION METHOD THEREOF AND USE THEREOF

(71) Applicant: CHENGDU BAIYU PHARMACEUTICAL CO., LTD, Chengdu, Sichuan (CN)

(72) Inventor: Yi Sun, Chengdu (CN)

(73) Assignee: CHENGDU BAIYU PHARMACEUTICAL CO., LTD, Chengdu (CN)

( * ) Notice: Subject to any disclaimer, the term of this patent is extended or adjusted under 35 U.S.C. 154(b) by 0 days.

(21) Appl. No.: 15/523,239

(22) PCT Filed: Oct. 30, 2015

(86) PCT No.: PCT/CN2015/093305
§ 371 (c)(1),
(2) Date: Apr. 28, 2017

(87) PCT Pub. No.: WO2016/066128
PCT Pub. Date: May 6, 2016

(65) Prior Publication Data
US 2017/0319542 A1 Nov. 9, 2017

(30) Foreign Application Priority Data
Oct. 30, 2014 (CN) .......................... 2014 1 0606703

(51) Int. Cl.
*A61K 31/365* (2006.01)
*A61K 31/423* (2006.01)
*A61K 31/444* (2006.01)
*A61K 31/4418* (2006.01)
*A61K 31/4545* (2006.01)
*A61K 31/5377* (2006.01)
*A61K 9/00* (2006.01)
*A61K 31/437* (2006.01)
*A61K 31/44* (2006.01)
*A61K 45/06* (2006.01)
*A61K 31/4425* (2006.01)
*A61P 7/02* (2006.01)

(52) U.S. Cl.
CPC .............. *A61K 31/365* (2013.01); *A61K 9/00* (2013.01); *A61K 31/423* (2013.01); *A61K 31/437* (2013.01); *A61K 31/44* (2013.01); *A61K 31/444* (2013.01); *A61K 31/4418* (2013.01); *A61K 31/4425* (2013.01); *A61K 31/4545* (2013.01); *A61K 31/5377* (2013.01); *A61K 45/06* (2013.01); *A61P 7/02* (2018.01)

(58) Field of Classification Search
CPC ................ A61K 31/365; A61K 31/423; A61K 31/4418; A61K 31/444; A61K 31/4545; A61K 31/5377
See application file for complete search history.

(56) References Cited

U.S. PATENT DOCUMENTS 4,734,280 A * 3/1988 Braquet ............... A61K 31/365
424/752
2004/0242660 A1* 12/2004 Straub .................. A61K 31/421
514/376

FOREIGN PATENT DOCUMENTS

| CN | 1759828 A | * | 4/2006 |
| CN | 1759828 A | | 4/2006 |
| CN | 102058889 A | | 5/2011 |
| KR | 10-2004-0020058 | | 3/2004 |

OTHER PUBLICATIONS

Feb. 2, 2016 Search Report issued in International Patent Application No. PCT/CN2015/093305.
Feb. 2, 2016 Written Opinion issued in International Patent Application No. PCT/CN2015/093305.
Jan. 9, 2018 Office Action issued in Japanese Patent Application No. 2017-542250.
Wong, Pancras C. et al. "Razaxaban, a Direct Factor Xa Inhibitor, in Combination with Aspirin and/or Clopidogrel Improves Low-Dose Antithrombotic Activity Without Enhancing Bleeding Liability in Rabbits" Journal of Thrombosis and Thrombolysis; vol. 24, Issue 1, 2007, pp. 43-51.
Takagaki, Ryoji. "Properties and Uses of Ginkgo biloba Leaf Extract". New Food Industry, vol. 40, No. 5, 1998, pp. 1-7.
Wada, Hideo et al. "Advance of Anti-Thrombotic and Anti-Coagulant Therapy". History of Medicine, vol. 242, No. 2, Jul. 2012, pp. 194-198.
Apr. 24, 2018 Office Action issued in Japanese Patent Application No. 2017-542250.
May 15, 2018 Extended European Search Report issued in European Patent Application No. 15854130.0.
Jun. 18, 2018 Office Action issued in Korean Patent Application No. 10-2017-7014595.
Koch, E. "Inhibition of Platelet Activating Factor (PAF)—Induced Aggregation of Human Thrombocytes by Ginkgolides: Considerations on Possible Bleeding Complications After Oral Intake of Ginkgo Biloba Extracts". Phytomedicine, vol. 12, No. 1-2, pp. 10-16, Jan. 10, 2005.
De Candia, Modesto, et al. "Novel Factor Xa Inhibitors: A Patent Review". Expert Opinion on Therapeutic Patents, vol. 19, No. 11, pp. 1535-1580, Nov. 1, 2009.
Mahan, Charles E. et al. "Performance of New Anticoagulants for Thromboprophylaxis in Patients Undergoing Hip and Knee Replacement Surgery". Pharmacotherapy, vol. 32, No. 11, pp. 1036-1048, Nov. 2012.

(Continued)

*Primary Examiner* — Sarah Pihonak
(74) *Attorney, Agent, or Firm* — Oliff PLC

(57) ABSTRACT

A pharmaceutical composition containing ginkgolide B and an Xa factor inhibitor xaban, a preparation method and use of the pharmaceutical composition, wherein the xaban is selected from Rivaroxaban, Apixaban, Edoxaban, Razaxaban and Otamixaban.

6 Claims, No Drawings

(56) References Cited

OTHER PUBLICATIONS

Trujillo, Toby et al. "Clinical Use of Rivaroxaban: Pharmacokinetic and Pharmacodynamic Rationale for Dosing Regimens in Different Indications". Drugs, vol. 74, No. 14, pp. 1587-1603, Sep. 1, 2014.
Paikin, Jeremy S. et al. "Effectiveness and Safety of Combined Antiplatelet and Anticoagulant Therapy: A Critical Review of the Evidence from Randomized Controlled Trials". Blood Reviews, vol. 25, No. 3, pp. 123-129, May 1, 2011.

* cited by examiner

PHARMACEUTICAL COMPOSITION CONTAINING GINKGOLIDE B AND XA FACTOR INHIBITOR, PREPARATION METHOD THEREOF AND USE THEREOF

TECHNICAL FIELD

The invention relates to a pharmaceutical composition containing Ginkgolide B and Xa factor inhibitor, preparation method and use thereof.

BACKGROUND OF THE INVENTION

In recent years, the development of novel anticoagulant drug, factor Xa inhibitor initiated a new direction for anticoagulant treatment. The factor Xa inhibitor not only increases the anticoagulant effect, but also reduces the risk of hemorrhage. It does not need blood monitoring, and is convenient for long-term treatment. Studies show that factor Xa plays an important role in controlling thrombin formation and activating blood coagulation cascade. Anti-coagulation effect is even stronger if the upstream factors of the coagulation cascade is inhibited. Factor Xa cannot activate platelets, and does not have positive feedback effect on the coagulation cascade. Direct factor Xa inhibitor can not only inhibit the factors associated with thrombus, but also inhibit the factors associated with prothrombin.

Rivaroxaban is the first factor Xa inhibitor on the market. Numbers of clinical research show that rivaroxaban is prior than the standard medicine Enoxaparin Sodium on preventing and treating venous thrombosis embolism. Rivaroxaban is clinically used to prevent deep venous thrombosis (DVT) and pulmonary embolism (PE) after hip and knee replacement surgery. It can prevent cerebral apoplexy and non-central nervous system embolism in patients with non-valve atrial fibrillation, reduce the risk of palindromia of coronary syndrome, and the like. However, overdosing can lead to bleeding complications due to the pharmacodynamics properties of Rivaroxaban. The bleeding risk of patients within certain sub-groups is high and specific antidote has not been developed.

Apixaban is an oral selective factor Xa activation inhibitor, a variation of Razaxaban. Developed by the collaboration of Pfizer and Bristol-Myers Squibb, it is now available on America and European Union market. It can prevent thrombus, especially for patients taken hip or knee replacement operation. However, among patients with acute coronary syndrome, researchers found that Apixaban may lead to increased dose-dependent bleeding cases and reduced ischemic cases, when applied together with anti-platelet treatment. The safety and effectiveness of Apixaban may depend on the basic anti-platelet treatment.

Edoxaban is a small molecule oral anticoagulation medicine developed by the Daiichi Sankyo in Japan. It is a blood clotting factor X (FXa) blocker and is used for treating concurrent venous thromboembolism (VTE) in patients taken total knee replacement (TKA), total hip replacement (THA) and hip fracture surgery (HFS). In the coagulation process, activated clotting factors X (FXa) activates prothrombin (FII) into thrombin (FIIa), which promotes the formation of fibrin and thrombus. Therefore, FXa has become a main target for the development of new generation of anti-coagulation medicine. Edoxaban inhibits the formation of thrombus by selectively, reversibility and directly inhibiting FXa. It is 104 times more selective to FXa compared to FIIa. Clinical studies in Japan or abroad all prove that Edoxaban can effectively and reliably inhibit concurrent VTE in patients taken lower limb orthopaedic surgery. However, its high cost is a limitation of this medicine, which may be an issue for most patients.

The relative molecular weight of Razaxaban is 528. Being as an effective oral peptide analogue, it has a high affinity with factor Xa. A phase II clinical study shows that it is effective in preventing venous thromboembolism (VTE) after orthopedic surgery. This is a random double-blind study and 656 patients taken total knee replacement operation participate. Among 438 effective patients, Razaxaban and VTE occurrence are in a dose-dependent manner. Notably, the VTE occurrence rate of patients taking Razaxaban 25 mg is significantly lower than that of patients taking enoxaparin, while the occurrence rate of large bleeding is similar between the two groups. However, patients taking Razaxaban 50-100 mg are more likely to have large bleeding compared to patients taking Enoxaparin.

Otamixaban is a thrombin factor Xa inhibitor for injection with high-selectivity and reversibility. It inhibits the formation of thrombus through a dose-dependent manner, with rapid effect-acting and loss of efficacy period. Its pharmacokinetic follows the linear pattern and is not easy to be eliminated through kidney. Previous studies show that treating ACS using activated X factor inhibitor has the risk of thrombus formation. Therefore, it should be noted in PCI operation that the dose of the anticoagulation drugs and other additional antithrombotic factors should be adjusted. However, the use of medium doses of Otamixaban appears to be free of these concerns. In addition, as Otamixaban has many advantages including rapid effect onset and loss of efficacy, intravenous administration and predictable anticoagulanting reaction (needn't monitor), Otamixaban can be the only anticoagulant medicine for NSTE-ACS patients from emergency treatment to interventional therapy, which is a great advantage. Other studies reported that Otamixaban excretion through kidney is less than 25%. Thus, the dosage for patients with impaired renal function does not need to be adjusted. It is also reported that Otamixaban cannot reduce the occurrence of ischemic cases and can increase the bleeding risk. So, it suggested not using Otamixaban on NSTE-ACS patients taking early PCI operation.

Therefore, how to reduce the massive use of Xaban medicine to reduce side effect and how to reduce the cost need to be resolved.

SUMMARY OF THE INVENTION

The invention aims to overcome the high risk of bleeding and other defect when using factor Xa inhibitor and provide a novel pharmaceutical composition as a new choice for patients.

The present invention provides a pharmaceutical composition comprising Ginkgolide B, which contains Ginkgolide B and factor Xa inhibitor, Wherein the factor Xa inhibitor is xaban type drug;

Wherein the xaban type drug is Rivaroxaban, Apixaban, Edoxaban, Razaxaban and/or Otamixaban.

The chemical structure of Rivaroxaban:

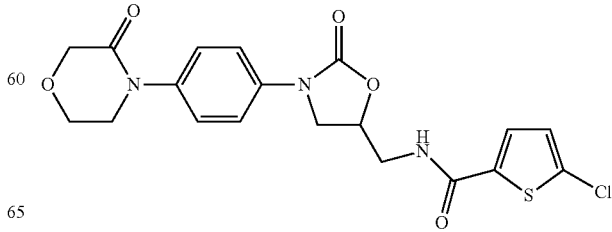

The chemical structure of Apixaban:

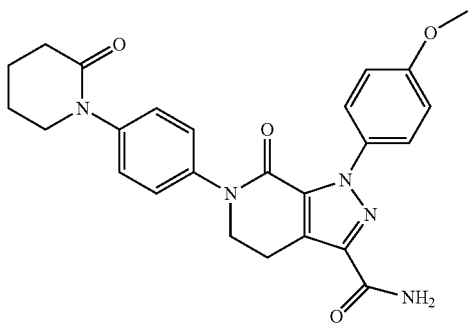 [SMILES: COc1ccc(-n2nc(C(N)=O)c3c2C(=O)N(c2ccc(N4CCCCC4=O)cc2)CC3)cc1]

The chemical structure of Edoxaban:

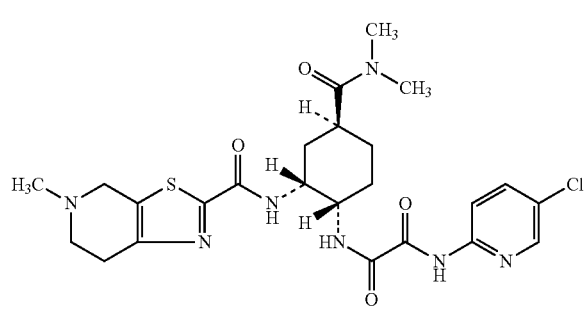

The chemical structure of Razaxaban:

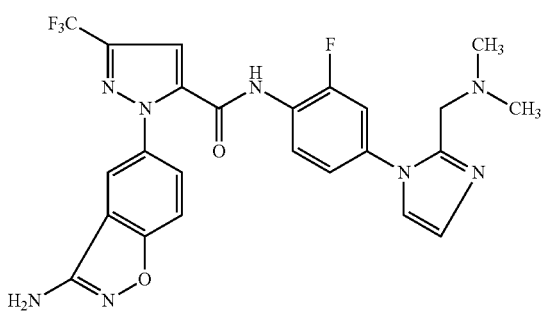 [SMILES: CN(C)Cc1nccn1-c1ccc(NC(=O)c2cc(C(F)(F)F)nn2-c2ccc3onc(N)c3c2)c(F)c1]

The chemical structure of Otamixaban:

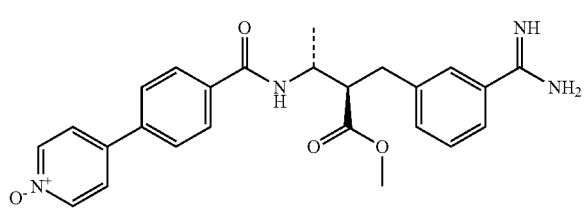

wherein Ginkgolide B is in an amount of 1-20 parts by weight, and Rivaroxaban is in an amount of 5-40 parts by weight;
preferably, Ginkgolide B is in an amount of 5-15 parts by weight and Rivaroxaban is in an amount of 10-20 by weight;
more preferably, Ginkgolide B is in an amount of 10 parts by weight and Rivaroxaban is in an amount of 15 parts by weight; or Ginkgolide B is in an amount of 1-20 parts by weight, and Apixaban is in an amount of 0.5-20 parts by weight;
preferably, Ginkgolide B is in an amount of 5-15 parts by weight and Apixaban is in an amount of 1-10 by weight;
more preferably, Ginkgolide B is in an amount of 10 parts by weight and Apixaban is in an amount of 5 parts by weight; or Ginkgolide B is in an amount of 1-20 parts by weight, and Edoxaban is in an amount of 8-50 parts by weight;
preferably, Ginkgolide B is in an amount of 5-15 parts by weight and Edoxaban is in an amount of 10-30 by weight;
more preferably, Ginkgolide B is in an amount of 10 parts by weight and Edoxaban is in an amount of 15 parts by weight; or Ginkgolide B is in an amount of 1-20 parts by weight, and Razaxaban is in an amount of 1-20 parts by weight;
preferably, Ginkgolide B is in an amount of 5-15 parts by weight and Razaxaban is in an amount of 5-15 by weight;
more preferably, Ginkgolide B is in an amount of 10 parts by weight and Razaxaban is in an amount of 10 parts by weight; or Ginkgolide B is in an amount of 1-20 parts by weight, and Otamixaban is in an amount of 15-150 parts by weight;
preferably, Ginkgolide B is in an amount of 5-15 parts by weight and Otamixaban is in an amount of 30-125 by weight; more preferably, Ginkgolide B is in an amount of 8-12 parts by weight and Otamixaban is in an amount of 50-90 parts by weight; even more preferably, Ginkgolide B is in an amount of 10 parts by weight and Otamixaban is in an amount of 60 parts by weight.

The present invention also provides a method for preparing the pharmaceutical composition, comprising the following steps:

S1: weighing out raw materials of Ginkgolide B and a factor Xa inhibitor xaban type drug according to the predetermined parts by weight; and S2: mixing the raw materials, and adding a pharmaceutically acceptable auxiliary to the raw materials to prepare a common pharmaceutical preparation.

Wherein the pharmaceutical acceptable auxiliary is selected from the group consisting of: starch, pregelatinized starch, lactose, sucrose, talcum powder, dextrin, cyclodextrin, microcrystalline cellulose, croscarmellose sodium, sodium carboxymethyl starch, low substituted hydroxypropyl cellulose, cross-linked povidone, glucose, meglumine, magnesium stearate, dextran, glycerol, ethanol, propylene glycol, polyethylene glycol, mannitol, sorbitol, xylitol, fiber vegetable oil, sodium benzoate, sodium salicylate, hydrochloric acid, citric acid, sodium citrate, sodium dihydrogen phosphate, disodium hydrogen phosphate, gelatin, lecithin and vitamin C.

Wherein the pharmaceutical formulation comprises: tablet, capsule, soft capsule, oral liquid, granules, pills, dripping pills, powder, paste, pellets, injections, suppository, patch, drop, spray, cream, suspension, tincture, emulsion, solution injection, powder injection, targeting formulation, sustained-release formulation and controlled-release formulation.

The present invention provides use of a pharmaceutical combination of Ginkgolide B and factor Xa inhibitor in the manufacture of a medicament for anti-platelet aggregation.

Wherein the factor Xa inhibitor is xaban type drug;
Wherein the xaban type drug is Rivaroxaban, Apixaban, Edoxaban, Razaxaban and/or Otamixaban.
wherein Ginkgolide B is in an amount of 1-20 parts by weight, and Rivaroxaban is in an amount of 5-40 parts by weight;

preferably, Ginkgolide B is in an amount of 5-15 parts by weight and Rivaroxaban is in an amount of 10-20 by weight; more preferably, Ginkgolide B is in an amount of 10 parts by weight and Rivaroxaban is in an amount of 15 parts by weight; or Ginkgolide B is in an amount of 1-20 parts by weight, and Apixaban is in an amount of 0.5-20 parts by weight;

preferably, Ginkgolide B is in an amount of 5-15 parts by weight and Apixaban is in an amount of 1-10 by weight; more preferably, Ginkgolide B is in an amount of 10 parts by weight and Apixaban is in an amount of 5 parts by weight; or Ginkgolide B is in an amount of 1-20 parts by weight, and Edoxaban is in an amount of 8-50 parts by weight;

preferably, Ginkgolide B is in an amount of 5-15 parts by weight and Edoxaban is in an amount of 10-30 by weight; more preferably, Ginkgolide B is in an amount of 10 parts by weight and Edoxaban is in an amount of 15 parts by weight; or Ginkgolide B is in an amount of 1-20 parts by weight, and Razaxaban is in an amount of 1-20 parts by weight;

preferably, Ginkgolide B is in an amount of 5-15 parts by weight and Razaxaban is in an amount of 5-15 by weight; more preferably, Ginkgolide B is in an amount of 10 parts by weight and Razaxaban is in an amount of 10 parts by weight; or Ginkgolide B is in an amount of 1-20 parts by weight, and Otamixaban is in an amount of 15-150 parts by weight;

preferably, Ginkgolide B is in an amount of 5-15 parts by weight and Otamixaban is in an amount of 30-125 by weight; more preferably, Ginkgolide B is in an amount of 8-12 parts by weight and Otamixaban is in an amount of 50-90 parts by weight; even more preferably, Ginkgolide B is in an amount of 10 parts by weight and Otamixaban is in an amount of 60 parts by weight.

The pharmaceutical composition of the present invention comprising Ginkgolide B and xaban as active ingredients, which function through different mechanisms for anti-platelet aggregation and can remarkably promote the anti-platelet aggregation function of Ginkgolide B and xaban type drug like Rivaroxaban, Apixaban, Edoxaban, Razaxaban and/or Otamixaban. Using Ginkgolide B and xaban drug results in a synergisitic effect, less dosage of xaban drug in clinic, better potency, reducing cost and side effect and providing a better choice for clinical study. The pharmaceutical composition of the present invention is characterized in a novel formula, simple components, a clear action mechanism and a remarkable effect, and a large-scale industrial production can be realized.

Ginkgolide B and xaban drug are combined in the present invention, and synergistic effect and effective platelet aggregation inhibition are achieved. When used in clinic, less dosage of xaban is needed, resulting milder side effect originating from large dosage and reduced cost. The use of the pharmaceutical combination in clinic is quite promising.

The above disclosure of the present invention is further described in detail in the following embodiments. The following embodiments are for better understanding of the present invention, not to limit the invention to the preferred embodiment. Any technique derived from the present invention, falls into the protection scope of the present invention.

DETAILED DESCRIPTION OF EMBODIMENTS

The Ginkgolide B monomer of the present invention can be obtained by purchasing a commercially available product, or obtained by separating and purifying the Ginkgolide using an existing method; Rivaroxaban, Apixaban, Edoxaban, Razaxaban and Otamixaban can also be obtained by purchasing a commercially available product or synthesized by using an existing method. All monomeric compounds are consistent with the structure of corresponding reference substance, and the purity of all the monomer compounds is over 95% analyzed by HPLC.

Embodiment 1

10 parts by weight of Ginkgolide B,
15 parts by weight of Rivaroxaban,
Pharmaceutically acceptable auxiliary.
Mixing the raw materials, then adding pharmaceutically acceptable auxiliary to the raw materials to prepare tablet according to a conventional process.

Embodiment 2

5 parts by weight of Ginkgolide B,
20 parts by weight of Rivaroxaban,
Pharmaceutically acceptable auxiliary.
Mixing the raw materials, then adding pharmaceutically acceptable auxiliary to the raw materials to prepare capsule or soft capsule according to a conventional process.

Embodiment 3

15 parts by weight of Ginkgolide B,
10 parts by weight of Rivaroxaban,
Pharmaceutically acceptable auxiliary.
Mixing the raw materials, then adding pharmaceutically acceptable auxiliary to the raw materials to prepare pills according to a conventional process.

Embodiment 4

1 parts by weight of Ginkgolide B,
5 parts by weight of Rivaroxaban,
Pharmaceutically acceptable auxiliary.
Mixing the raw materials, then adding pharmaceutically acceptable auxiliary to the raw materials to prepare oral liquid according to a conventional process.

Embodiment 5

20 parts by weight of Ginkgolide B,
40 parts by weight of Rivaroxaban,
Pharmaceutically acceptable auxiliary.
Mixing the raw materials, then adding pharmaceutically acceptable auxiliary to the raw materials to prepare dripping pills according to a conventional process.

Embodiment 6

10 parts by weight of Ginkgolide B,
5 parts by weight of Apixaban,
Pharmaceutically acceptable auxiliary.
Mixing the raw materials, then adding pharmaceutically acceptable auxiliary to the raw materials to prepare spray according to a conventional process.

Embodiment 7

5 parts by weight of Ginkgolide B,
1 part by weight of Apixaban,
Pharmaceutically acceptable auxiliary.
Mixing the raw materials, then adding pharmaceutically acceptable auxiliary to the raw materials to prepare solution injection or powder injection according to a conventional process.

Embodiment 8

15 parts by weight of Ginkgolide B,
10 parts by weight of Apixaban,
Pharmaceutically acceptable auxiliary.

Mixing the raw materials, then adding pharmaceutically acceptable auxiliary to the raw materials to prepare sustained-release formulation and controlled-release formulation according to a conventional process.

Embodiment 9

20 parts by weight of Ginkgolide B,
20 parts by weight of Apixaban,
Pharmaceutically acceptable auxiliary.

Mixing the raw materials, then adding pharmaceutically acceptable auxiliary to the raw materials to prepare targeting formulation according to a conventional process.

Embodiment 10

10 parts by weight of Ginkgolide B,
15 parts by weight of Edoxaban,
Pharmaceutically acceptable auxiliary.

Mixing the raw materials, then adding pharmaceutically acceptable auxiliary to the raw materials to prepare granules or suspension according to a conventional process.

Embodiment 11

5 parts by weight of Ginkgolide B,
30 parts by weight of Edoxaban,
Pharmaceutically acceptable auxiliary.

Mixing the raw materials, then adding pharmaceutically acceptable auxiliary to the raw materials to prepare tablet according to a conventional process.

Embodiment 12

15 parts by weight of Ginkgolide B,
10 parts by weight of Edoxaban,
Pharmaceutically acceptable auxiliary.

Mixing the raw materials, then adding pharmaceutically acceptable auxiliary to the raw materials to prepare capsule or soft capsule according to a conventional process.

Embodiment 13

1 part by weight of Ginkgolide B,
8 parts by weight of Edoxaban,
Pharmaceutically acceptable auxiliary.

Mixing the raw materials, then adding pharmaceutically acceptable auxiliary to the raw materials to prepare pills according to a conventional process.

Embodiment 14

20 parts by weight of Ginkgolide B,
50 parts by weight of Edoxaban,
Pharmaceutically acceptable auxiliary.

Mixing the raw materials, then adding pharmaceutically acceptable auxiliary to the raw materials to prepare oral liquid according to a conventional process.

Embodiment 15

10 parts by weight of Ginkgolide B,
10 parts by weight of Razaxaban,
Pharmaceutically acceptable auxiliary.

Mixing the raw materials, then adding pharmaceutically acceptable auxiliary to the raw materials to prepare dripping pills according to a conventional process.

Embodiment 16

5 parts by weight of Ginkgolide B,
15 parts by weight of Razaxaban,
Pharmaceutically acceptable auxiliary.

Mixing the raw materials, then adding pharmaceutically acceptable auxiliary to the raw materials to prepare spray according to a conventional process.

Embodiment 17

15 parts by weight of Ginkgolide B,
5 parts by weight of Razaxaban,
Pharmaceutically acceptable auxiliary.

Mixing the raw materials, then adding pharmaceutically acceptable auxiliary to the raw materials to prepare solution injection or powder injection according to a conventional process.

Embodiment 18

1 part by weight of Ginkgolide B,
20 parts by weight of Razaxaban,
Pharmaceutically acceptable auxiliary.

Mixing the raw materials, then adding pharmaceutically acceptable auxiliary to the raw materials to prepare sustained-release formulation and controlled-release formulation according to a conventional process.

Embodiment 19

20 parts by weight of Ginkgolide B,
1 part by weight of Razaxaban,
Pharmaceutically acceptable auxiliary.

Mixing the raw materials, then adding pharmaceutically acceptable auxiliary to the raw materials to prepare targeting formulation according to a conventional process.

Embodiment 20

10 parts by weight of Ginkgolide B,
60 parts by weight of Otamixaban,
Pharmaceutically acceptable auxiliary.

Mixing the raw materials, then adding pharmaceutically acceptable auxiliary to the raw materials to prepare granules or suspension according to a conventional process.

Embodiment 21

8 parts by weight of Ginkgolide B,
50 parts by weight of Otamixaban,
Pharmaceutically acceptable auxiliary.

Mixing the raw materials, then adding pharmaceutically acceptable auxiliary to the raw materials to prepare oral liquid according to a conventional process.

Embodiment 22

12 parts by weight of Ginkgolide B,
90 parts by weight of Otamixaban,
Pharmaceutically acceptable auxiliary.

Mixing the raw materials, then adding pharmaceutically acceptable auxiliary to the raw materials to prepare dripping pills according to a conventional process.

Embodiment 23

15 parts by weight of Ginkgolide B,
125 parts by weight of Otamixaban,
Pharmaceutically acceptable auxiliary.

Mixing the raw materials, then adding pharmaceutically acceptable auxiliary to the raw materials to prepare spray according to a conventional process.

Embodiment 24

1 part by weight of Ginkgolide B,
15 parts by weight of Otamixaban,
Pharmaceutically acceptable auxiliary.

Mixing the raw materials, then adding pharmaceutically acceptable auxiliary to the raw materials to prepare solution injection or powder injection according to a conventional process.

Embodiment 25

20 parts by weight of Ginkgolide B,
125 parts by weight of Otamixaban,
Pharmaceutically acceptable auxiliary.

Mixing the raw materials, then adding pharmaceutically acceptable auxiliary to the raw materials to prepare sustained-release formulation and controlled-release formulation according to a conventional process.

The beneficial effects of the present invention are further described by following experimental examples.

Experimental Example 1

In Vitro Study of Composition of Ginkgolide B and Xaban Drug in Inhibition of Rabbit Platelet Aggregation Effect Under the Induction of PAF and Influence on the Activity of Factor Xa 1. Purpose of the Experiment Evaluation of the anti-platelet aggregation induced by PAF in vitro and the influence on the anti-factor Xa activity of Ginkgolide B and xaban type drug which are both manufactured by CHENGDU BAIYU TECHNOLOGY PHARMACY CO., LTD, by using turbidity microplate reader.

2. Materials and Methods 2.1. Experimental Animals:

SPF grade Japanese large-ear white rabbits with a weight of 2.2 kg-2.5 kg, half male and half female.

2.2 Experimental Medicine

Ginkgolide B (CHENGDU BAIYU TECHNOLOGY PHARMACY CO., LTD), Rivaroxaban (CHENGDU BAIYU TECHNOLOGY PHARMACY CO., LTD), Apixaban (CHENGDU BAIYU TECHNOLOGY PHARMACY CO., LTD), Edoxaban (CHENGDU BAIYU TECHNOLOGY PHARMACY CO., LTD), Razaxaban (CHENGDU BAIYU TECHNOLOGY PHARMACY CO., LTD), Otamixaban (CHENGDU BAIYU TECHNOLOGY PHARMACY CO., LTD), Composition 1 (Ginkgolide B:Rivaroxaban=10:15), Composition 2 (Ginkgolide B:Rivaroxaban=1:5), Composition 3 (Ginkgolide B:Rivaroxaban=1:40), Composition 4 (Ginkgolide B:Rivaroxaban=20:5), Composition 5 (Ginkgolide B:Rivaroxaban=20:40), Composition 6 (Ginkgolide B:Rivaroxaban=5:20), Composition 7 (Ginkgolide B:Rivaroxaban=15:10), Composition 8 (Ginkgolide B:Rivaroxaban=15:20), Composition 9 (Ginkgolide B:Apixaban=10:5), Composition 10 (Ginkgolide B:Apixaban=1:20), Composition 11 (Ginkgolide B:Apixaban=20:0.5), Composition 12 (Ginkgolide B:Apixaban=20:20), Composition 13 (Ginkgolide B:Apixaban=5:1), Composition 14 (Ginkgolide B:Apixaban=5:10), Composition 15 (Ginkgolide B:Apixaban=15:1), Composition 16 (Ginkgolide B:Apixaban=15:10), Composition 17 (Ginkgolide B:Edoxaban=10:15), Composition 18 (Ginkgolide B:Edoxaban=1:8), Composition 19 (Ginkgolide B:Edoxaban=1:50), Composition 20 (Ginkgolide B:Edoxaban=20:8), Composition 21 (Ginkgolide B:Edoxaban=20:50), Composition 22 (Ginkgolide B:Edoxaban=5:10), Composition 23 (Ginkgolide B:Edoxaban=15:10), Composition 24 (Ginkgolide B:Edoxaban=5:30), Composition 25 (Ginkgolide B:Razaxaban=10:10), Composition 26 (Ginkgolide B:Razaxaban=1:20), Composition 27 (Ginkgolide B:Razaxaban=20:1), Composition 28 (Ginkgolide B:Razaxaban=5:15), Composition 29 (Ginkgolide B:Razaxaban=15:5), Composition 30 (Ginkgolide B:Otamixaban=10:60), Composition 31 (Ginkgolide B:Otamixaban=1:15), Composition 32 (Ginkgolide B:Otamixaban=1:150), Composition 33 (Ginkgolide B:Otamixaban=20:15), Composition 34 (Ginkgolide B:Otamixaban=20:150), Composition 35 (Ginkgolide B:Otamixaban=15:30), Composition 36 (Ginkgolide B:Otamixaban=5:125), Composition 37 (Ginkgolide B:Otamixaban=15:125), Composition 38 (Ginkgolide B:Otamixaban=8:50), Composition 39 (Ginkgolide B:Otamixaban=8:90), Composition 40 (Ginkgolide B:Otamixaban=12:50), Composition 41 (Ginkgolide B:Otamixaban=12:90).

2.3 Reagents and Instruments

Instruments:

Electronic balance from Sartorius BS124S, Germany (accuracy: 0.0001 g), instrument number: BKY-YB-001; Electronic platform scale ACS-15LED from Shanghai Yingpai Scales Co., Ltd, instrument number: BKY-YB-002; DL-5M stand low-speed high-capacity freezing centrifuge from Changsha Xiangzhi, instrument number: BKY-ZX-040 produced by Changsha Xiangzhi Centrifuge Instrument Co., Ltd; Haier DW-40L188 low-temperature preservation box for preserving plasma and the like, instrument number: BKY-ZX-012; LSC-316C Xingxing stand storage cabinet for reagent storage, instrument number: BKY-ZX-041; Multiskan MK3 type microplate reader, instrument number BKY-ZX-014; Wellwash 4 MK2 microplate washer, instrument number: BKY-ZX-022; Transferpette® S, D-1000 Micropipettor from Brand, Germany, instrument number: BKY-ZX-036; Transferpette® S, D-100 Micropipettor from Brand, Germany, instrument number: BKY-ZX-038; MB-1830 full-automatic blood analyzer produced by Sichuan Meisheng technology Co. Ltd, instrument number: BKY-ZX-023.

Reagents:

3.8% sodium citrate (500 g/bottle, Kelong Chemical Reagents in Chengdu, lot number: 20130601); Platelet activation factors (PAF) (1 mg/bottle, Sigma, lot number: P7568); anti-coagulation factor (Xa) determination reagent (chromogenic substrate assay) (10×71 nkat, Italy Chromogenix, lot number: N1243555); polyethylene glycol (PEG) 6000 (50 g, Beijing J&K Scientific Ltd. lot number: LB50P76), heparin sodium (1 g/bottle, Bomei, lot number: 9041-08-1).

2.4 Dosage and Compositions

① All groups were administered with a dosage with different amounts of drug on the basis of clinically administration for anti-platelet aggregation. The dosage is showed in the following Table 1:

TABLE 1

Drug administration plan

| Group | Dosage | Daily dosing frequency |
|---|---|---|
| Saline | 2 ml | 1 |
| Ginkgolide B | 5.0 mg/kg | 1 |
| Rivaroxaban | 5.0 mg/kg | 1 |
| Apixaban | 5.0 mg/kg | 1 |
| Edoxaban | 5.0 mg/kg | 1 |
| Razaxaban | 5.0 mg/kg | 1 |
| Otamixaban | 5.0 mg/kg | 1 |
| Composition 1 | 5.0 mg/kg | 1 |
| Composition 2 | 5.0 mg/kg | 1 |
| Composition 3 | 5.0 mg/kg | 1 |
| Composition 4 | 5.0 mg/kg | 1 |
| Composition 5 | 5.0 mg/kg | 1 |
| Composition 6 | 5.0 mg/kg | 1 |
| Composition 7 | 5.0 mg/kg | 1 |
| Composition 8 | 5.0 mg/kg | 1 |
| Composition 9 | 5.0 mg/kg | 1 |
| Composition 10 | 5.0 mg/kg | 1 |
| Composition 11 | 5.0 mg/kg | 1 |
| Composition 12 | 5.0 mg/kg | 1 |
| Composition 13 | 5.0 mg/kg | 1 |
| Composition 14 | 5.0 mg/kg | 1 |
| Composition 15 | 5.0 mg/kg | 1 |
| Composition 16 | 5.0 mg/kg | 1 |
| Composition 17 | 5.0 mg/kg | 1 |
| Composition 18 | 5.0 mg/kg | 1 |
| Composition 19 | 5.0 mg/kg | 1 |
| Composition 20 | 5.0 mg/kg | 1 |
| Composition 21 | 5.0 mg/kg | 1 |
| Composition 22 | 5.0 mg/kg | 1 |
| Composition 23 | 5.0 mg/kg | 1 |
| Composition 24 | 5.0 mg/kg | 1 |
| Composition 25 | 5.0 mg/kg | 1 |
| Composition 26 | 5.0 mg/kg | 1 |
| Composition 27 | 5.0 mg/kg | 1 |
| Composition 28 | 5.0 mg/kg | 1 |
| Composition 29 | 5.0 mg/kg | 1 |
| Composition 30 | 5.0 mg/kg | 1 |
| Composition 31 | 5.0 mg/kg | 1 |
| Composition 32 | 5.0 mg/kg | 1 |
| Composition 33 | 5.0 mg/kg | 1 |
| Composition 34 | 5.0 mg/kg | 1 |
| Composition 35 | 5.0 mg/kg | 1 |
| Composition 36 | 5.0 mg/kg | 1 |
| Composition 37 | 5.0 mg/kg | 1 |
| Composition 38 | 5.0 mg/kg | 1 |
| Composition 39 | 5.0 mg/kg | 1 |
| Composition 40 | 5.0 mg/kg | 1 |
| Composition 41 | 5.0 mg/kg | 1 |

2.5 Study of Platelet Aggregation Rate

Blood was taken by puncture from the heart of animals, subjected to 3.8% sodium citrate at 1:9 for anticoagulation, then centrifuged for 10 minutes at 1000 r/min at 4° C. and platelet-rich plasma (PRP) was collected, and the remaining portion was centrifuged for 15 min at a speed of 3000 r/min for obtaining platelet-depleted plasma (PPP). PPP was used to adjust the number of platelet in PRP, to be at $200\pm50\times10^9$/L.

250 μl of PRP was added to the holes of a microreaction plate and then 10 μl of the predetermined concentration of medicine was added. Each concentration of medicine was added to two parallel holes and then 10 μl of PAF (0.38 μg/ml) of platelet aggregation agent was added into the holes; 250 μl of PPP and 10 μl of saline was added to the blank control hole; 250 μl of PPP and 10 μl of dimethyl sulfoxide was added to the solvent control hole. The absorbance at different times was recorded until the absorbance is no longer reduced, indicating the time to reach maximum aggregation of platelets, and then the inhibition rate of the blood platelets is calculated by using the following formula:

The aggregation inhibition rate=(the maximum aggregation time of drug group−the maximum aggregation of the blank control group)/the maximum aggregation of the blank control group×100%

2.6 Activity of Anti-Coagulation Factor Xa

A chromogenic substrate assay was adopted, and plasma anti-Xa activity was determined on a microplate reader according to a kit specification and reference documents.

2.7 Statistical Analysis:

The experimental results were used to calculate the aggregation inhibition rate and the anti-Xa activity, according to a corresponding calculation formula, the excel software was adopted to calculate the average.

3. Results 3.1 Platelet Aggregation Experiment Result

TABLE 2

The anti PAF-induced platelet aggregation in vitro of combination of Ginkgolide B and xaban (n = 2)

| Group | Platelet max aggregation time (min) | Platelet aggregation inhibition rate (%) |
|---|---|---|
| Saline | 20 | — |
| Ginkgolide B | 30 | 50 |
| Rivaroxaban | 25 | 25 |
| Apixaban | 40 | 100 |
| Edoxaban | 30 | 80 |
| Razaxaban | 35 | 75 |
| Otamixaban | 40 | 100 |
| Composition 1 | 60 | 200 |
| Composition 2 | 30 | 50 |
| Composition 3 | 35 | 75 |
| Composition 4 | 33 | 65 |
| Composition 5 | 55 | 175 |
| Composition 6 | 50 | 150 |
| Composition 7 | 56 | 180 |
| Composition 8 | 59 | 195 |
| Composition 9 | 88 | 340 |
| Composition 10 | 44 | 120 |
| Composition 11 | 48 | 140 |
| Composition 12 | 45 | 125 |
| Composition 13 | 60 | 200 |
| Composition 14 | 65 | 225 |
| Composition 15 | 68 | 240 |
| Composition 16 | 75 | 275 |
| Composition 17 | 80 | 300 |
| Composition 18 | 50 | 150 |
| Composition 19 | 60 | 200 |
| Composition 20 | 65 | 225 |
| Composition 21 | 66 | 230 |
| Composition 22 | 76 | 280 |
| Composition 23 | 79 | 295 |
| Composition 24 | 73 | 265 |
| Composition 25 | 60 | 200 |
| Composition 26 | 36 | 80 |
| Composition 27 | 40 | 100 |
| Composition 28 | 55 | 175 |
| Composition 29 | 58 | 190 |
| Composition 30 | 90 | 350 |
| Composition 31 | 50 | 150 |
| Composition 32 | 55 | 175 |
| Composition 33 | 52 | 160 |
| Composition 34 | 65 | 225 |
| Composition 35 | 62 | 210 |
| Composition 36 | 60 | 200 |
| Composition 37 | 58 | 190 |
| Composition 38 | 79 | 295 |
| Composition 39 | 85 | 325 |
| Composition 40 | 80 | 300 |
| Composition 41 | 83 | 315 |

From table 2, one can see that there was a significant difference in the platelet aggregation rate of all composition groups when comparing with the saline group under the induction of PAF (p<0.01, p<0.05), indicating the pharmaceutical compositions of the present invention can effectively inhibit the aggregation of platelet. When using Ginkgolide B and xaban drug together, the anti-platelet aggregation activity was remarkably improved comparing to the activity of using Ginkgolide B or xaban drug alone, indicating the Ginkgolide B and xaban drug work synergistically.

3.2 Anti-Factor Xa Activity Result

TABLE 3

The anti-factor X a activity of combination of Ginkgolide B and xaban in vitro

| Group | Anti-factor X a activity (IU/ml) |
|---|---|
| Saline | 0 |
| Ginkgolide B | 0.57 |
| Rivaroxaban | 0.54 |
| Apixaban | 1.07 |
| Edoxaban | 0.79 |
| Razaxaban | 0.86 |
| Otamixaban | 1.03 |
| Composition 1 | 1.53 |
| Composition 2 | 0.95 |
| Composition 3 | 1.06 |
| Composition 4 | 0.96 |
| Composition 5 | 1.47 |
| Composition 6 | 1.04 |
| Composition 7 | 1.39 |
| Composition 8 | 1.45 |
| Composition 9 | 1.55 |
| Composition 10 | 0.87 |
| Composition 11 | 0.92 |
| Composition 12 | 1.11 |
| Composition 13 | 1.50 |
| Composition 14 | 1.38 |
| Composition 15 | 1.45 |
| Composition 16 | 1.52 |
| Composition 17 | 1.45 |
| Composition 18 | 1.01 |
| Composition 19 | 0.98 |
| Composition 20 | 1.10 |
| Composition 21 | 0.85 |
| Composition 22 | 1.39 |
| Composition 23 | 1.40 |
| Composition 24 | 1.35 |
| Composition 25 | 1.52 |
| Composition 26 | 0.96 |
| Composition 27 | 0.91 |
| Composition 28 | 1.46 |
| Composition 29 | 1.39 |
| Composition 30 | 1.56 |
| Composition 31 | 1.11 |
| Composition 32 | 0.96 |
| Composition 33 | 1.89 |
| Composition 34 | 0.98 |
| Composition 35 | 1.15 |
| Composition 36 | 1.06 |
| Composition 37 | 1.17 |
| Composition 38 | 1.49 |
| Composition 39 | 1.52 |
| Composition 40 | 1.38 |
| Composition 41 | 1.50 |

Note:
An effective anticoagulation is defined as plasma anti-factor X a activity ≥0.5 IU/ML (reported by "The use of low-molecular-weight heparin on patients with cardiovascular disease should be scandalized", according to the pharmacokinetic of LMWH in vivo).

From table 3, one can see that there was a significant difference in the anti-factor Xa activity of all composition groups when comparing with the saline group, indicating the pharmaceutical compositions of the present invention can effectively inhibit the activity of factor Xa and aggregation of platelet. When using Ginkgolide B and xaban drug together, the anti-factor Xa activity was remarkably improved comparing to the activity of using Ginkgolide B or xaban drug alone, indicating the Ginkgolide B and xaban drug work synergistically.

From table 2 and 3, one can see that among the compositions comprising Ginkgolide B and Rivaroxaban (Composition 1-8), the aggregation inhibition rate and the anti-factor Xa activity of composition 1, 5-8 are relatively higher, while the aggregation inhibition rate and the anti-factor Xa activity of composition 1 are the highest. Therefore, among the compositions comprising Ginkgolide B and Rivaroxaban, preferably, Ginkgolide B is in an amount of 5-15 parts by weight and Rivaroxaban is in an amount of 10-20 by weight; most preferably, Ginkgolide B is in an amount of 10 parts by weight and Rivaroxaban is in an amount of 15 parts by weight.

Among the compositions comprising Ginkgolide B and Apixaban (Composition 9-16), the aggregation inhibition rate and the anti-factor Xa activity of composition 9, 13-16 are relatively higher, while the aggregation inhibition rate and the anti-factor Xa activity of composition 9 are the highest. Therefore, among the compositions comprising Ginkgolide B and Apixaban, preferably, Ginkgolide B is in an amount of 5-15 parts by weight and Apixaban is in an amount of 1-10 by weight; most preferably, Ginkgolide B is in an amount of 10 parts by weight and Apixaban is in an amount of 5 parts by weight.

Among the compositions comprising Ginkgolide B and Edoxaban (Composition 17-24), the aggregation inhibition rate and the anti-factor Xa activity of composition 17, 22-24 are relatively higher, while the aggregation inhibition rate and the anti-factor Xa activity of composition 17 are the highest. Therefore, among the compositions comprising Ginkgolide B and Edoxaban, preferably, Ginkgolide B is in an amount of 5-15 parts by weight and Edoxaban is in an amount of 10-30 by weight; most preferably, Ginkgolide B is in an amount of 10 parts by weight and Edoxaban is in an amount of 15 parts by weight.

Among the compositions comprising Ginkgolide B and Razaxaban (Composition 25-29), the aggregation inhibition rate and the anti-factor Xa activity of composition 25, 28-29 are relatively higher, while the aggregation inhibition rate and the anti-factor Xa activity of composition 25 are the highest. Therefore, among the compositions comprising Ginkgolide B and Razaxaban, preferably, Ginkgolide B is in an amount of 5-15 parts by weight and Razaxaban is in an amount of 5-15 by weight; most preferably, Ginkgolide B is in an amount of 10 parts by weight and Razaxaban is in an amount of 10 parts by weight.

Among the compositions comprising Ginkgolide B and Otamixaban (Composition 30-41), the aggregation inhibition rate and the anti-factor Xa activity of composition 30, 38-41 are relatively higher, while the aggregation inhibition rate and the anti-factor Xa activity of composition 30 are the highest. Therefore, among the compositions comprising Ginkgolide B and Otamixaban, preferably, Ginkgolide B is in an amount of 8-12 parts by weight and Otamixaban is in an amount of 50-90 parts by weight; most preferably, Ginkgolide B is in an amount of 10 parts by weight and Otamixaban is in an amount of 10 parts by weight.

The experimental results showed that the combination of Ginkgolide B and xaban type drug like Rivaroxaban, Apixaban, Edoxaban, Razaxaban or Otamixaban as active ingredients can remarkably promote the anti-platelet aggregation and anti-factor Xa activity. Combined usage of Ginkgolide B and xaban drug results in a synergistic effect and is better than using Ginkgolide B or xaban drug alone. Combined usage of Ginkgolide B and xaban drug function through different mechanisms and can remarkably promote the anti-platelet aggregation and anti-factor Xa activity.

Experimental Example 2

A Comparative Study on the Anti-Coagulating Effect and Anti-Coagulating Factor Activity of Ginkgolide B and Xaban Drug by Using Rabbit Wound-Limb Deep Venous Thrombosis Forming Model.

1. Purpose of the Experiment

Compare the difference on the anti-coagulating effect and anti-coagulating factor activity of Ginkgolide B and Xaban by using rabbit wound-limb deep venous thrombosis forming model.

2. Materials and Methods 2.1. Experimental Animals:

Grade I(CV) male Japanese large-ear white rabbits with a weight of 2.0 kg-3.0 kg, 8 rabbits in each group.

2.2 Experimental Medicine

Ginkgolide B (CHENGDU BAIYU TECHNOLOGY PHARMACY CO., LTD), Rivaroxaban (CHENGDU BAIYU TECHNOLOGY PHARMACY CO., LTD), Apixaban (CHENGDU BAIYU TECHNOLOGY PHARMACY CO., LTD), Edoxaban (CHENGDU BAIYU TECHNOLOGY PHARMACY CO., LTD), Razaxaban (CHENGDU BAIYU TECHNOLOGY PHARMACY CO., LTD), Otamixaban (CHENGDU BAIYU TECHNOLOGY PHARMACY CO., LTD), Composition 1 (Ginkgolide B:Rivaroxaban=10:15), Composition 2 (Ginkgolide B:Rivaroxaban=1:5), Composition 3 (Ginkgolide B:Rivaroxaban=1:40), Composition 4 (Ginkgolide B:Rivaroxaban=20:5), Composition 5 (Ginkgolide B:Rivaroxaban=20:40), Composition 6 (Ginkgolide B:Rivaroxaban=5:20), Composition 7 (Ginkgolide B:Rivaroxaban=15:10), Composition 8 (Ginkgolide B:Rivaroxaban=15:20), Composition 9 (Ginkgolide B:Apixaban=10:5), Composition 10 (Ginkgolide B:Apixaban=1:20), Composition 11 (Ginkgolide B:Apixaban=20:0.5), Composition 12 (Ginkgolide B:Apixaban=20:20), Composition 13 (Ginkgolide B:Apixaban=5:1), Composition 14 (Ginkgolide B:Apixaban=5:10), Composition 15 (Ginkgolide B:Apixaban=15:1), Composition 16 (Ginkgolide B:Apixaban=15:10), Composition 17 (Ginkgolide B:Edoxaban=10:15), Composition 18 (Ginkgolide B:Edoxaban=1:8), Composition 19 (Ginkgolide B:Edoxaban=1:50), Composition 20 (Ginkgolide B:Edoxaban=20:8), Composition 21 (Ginkgolide B:Edoxaban=20:50), Composition 22 (Ginkgolide B:Edoxaban=5:10), Composition 23 (Ginkgolide B:Edoxaban=15:10), Composition 24 (Ginkgolide B:Edoxaban=5:30), Composition 25 (Ginkgolide B:Razaxaban=10:10), Composition 26 (Ginkgolide B:Razaxaban=1:20), Composition 27 (Ginkgolide B:Razaxaban=20:1), Composition 28 (Ginkgolide B:Razaxaban=5:15), Composition 29 (Ginkgolide B:Razaxaban=15:5), Composition 30 (Ginkgolide B:Otamixaban=10:60), Composition 31 (Ginkgolide B:Otamixaban=1:15), Composition 32 (Ginkgolide B:Otamixaban=1:150), Composition 33 (Ginkgolide B:Otamixaban=20:15), Composition 34 (Ginkgolide B:Otamixaban=20:150), Composition 35 (Ginkgolide B:Otamixaban=15:30), Composition 36 (Ginkgolide B:Otamixaban=5:125), Composition 37 (Ginkgolide B:Otamixaban=15:125), Composition 38 (Ginkgolide B:Otamixaban=8:50), Composition 39 (Ginkgolide B:Otamixaban=8:90), Composition 40 (Ginkgolide B:Otamixaban=12:50), Composition 41 (Ginkgolide B:Otamixaban=12:90).

2.3 Reagents and Instruments

Instruments:

(1) Rabbits Weighing Instruments:

Electronic platform scale ACS-15LED is from Shanghai Yingpai Scales Co., Ltd, with the resolution of 1 g, and maximum weighing of 6 kg, for weighting rabbits.

(2) Coagulation and Coagulation Factor Activity Analyzing Instrument

Sysmex CA-660 full-automatic blood coagulation analyzer, instrument number: BKY-ZX-044, produced by the Sysmex Biotechnology Co. Ltd. (Wuxi)

DL-5M low-speed freezing centrifuge, instrument number: BKY-ZX-040 produced by Changsha Xiangzhi Centrifuge Instrument Co., Ltd.

BC-117F refrigerator, instrument number: BKY-ZX-015 produced by Haier Ltd. Inc., Qingdao.

(3) PAF Measuring Instrument

Multiskan MK3 microplate reader, instrument number: BKY-ZX-014 produced by Thermo Electron Corporation, USA.

(4) Pathological Examination Instrument

Sartorius BS124S electronic balance (index: 0.0001 g), instrument number: BKY-TJ-002, produced by Sartorius Inc., Germany.

ZT-14 V2 biological tissue automatic dehydrator, instrument number: BKY-BL-016, produced by Yaguang Medical Electronic Technology Co. Ltd. in Xiaogan.

Changzhou Zhongwei BMJ-III embedding machine, instrument number: BKY-BL-002, produced by Zhongwei Electronics Inc., Changzhou, Jiangsu.

Changzhou Zhongwei PHY-III pathological tissue bleaching and drying instrument, instrument serial number: BKY-BL-003, produced by Zhongwei Electronics Inc., Changzhou, Jiangsu.

Leica RM2126 rotary slicing machine, instrument number: BKY-BL-004, produced by Leica Biosystems, Co. Ltd., Shanghai.

Japan Olympus BX41-32P01 microscope, instrument number: BKY-BL-013, produced by Olympus Co., Japan.

YR-21 biological tissue automatic dying machine, instrument number: BKY-BL-015, produced by Yaguang Medical Electronic Technology Co. Ltd., Xiaogan, China.

Beijing Yongguangming 202-0 table drying box, instrument serial number: BKY-BL-005, produced by Yongguangming medical instruments, Beijing.

Reagents:

(1) Reagents Required for the Test

Hydroxypropyl methylcellulose (offered by delegation).

Lactose, specification: 100 g/bottle, lot number: 2015041701, expiration date: June 2018, Chengdu Kelong Chemical Reagent Company; Mannitol, specification: 500 g/bottle, lot number: 201402201, expire date: June 2017, Chengdu Kelong Chemical Reagent Company.

(2) Reagent for Testing Coagulation Function and Coagulation Factor Activity

Coagulation quality control, specification: 1 ml×10 bottle/box, lot number: 528167B, expiration date: Apr. 27, 2017, produced by SIEMENS.

PT reagent, specification: 2 ml×10 bottles/box, lot number: R5003/R5005, expiration date: Jan. 1, 2017/Mar. 1, 2017, produced by Sysmex Biotechnology Co. Ltd.

aPTT reagent, specification: 2 ml×10 bottles/box, lot number: R5001/R5006, expiration date: Sep. 1, 2016/Dec. 1, 2016, produced by Sysmex Biotechnology Co. Ltd.

Anti-coagulation factor (Xa) assay kit (chromogenic substrate method), specification: 10×71 nkat, lot number: N1243555, produced by Chromogenix, Italy.

Chromogenic substrate S, specification: 25 mg, lot number: N1143454, produced by Chromogenix, Italy.

Polyethylene glycol (PEG) 6000, specification: 50 g, lot number: LB50P76, produced by Beijing J&K Scientific Ltd.

Heparin sodium, specification: 1 g/bottle, lot number: 9041-08-1, produced by Bomei.

(3) PAF Content Testing Reagent

Experimental rabbit platelet activation factor (PAF) kit, specification: 96T/box×5 box, 48T/box×1 box, lot number: 201509, 201508, expiration date: February 2016, produced by Enzyme-linked Biotechnology Co., Ltd, Shanghai.

(4) Anesthesia Agent

Pentobarbital sodium is used for rabbit anesthesia. Diluted by purified water, pentobarbital sodium is prepared as 3% (g/v) solution concentration and is used when establishing the rabbit model.

(5) Pathological Inspection

Tissue specimen fixing solution (FAA solution):

95% ethanol (AR grade), lot number: 2015052301, expiration date: April 2020, specification: 20 kg/barrel, produced by Chengdu Kelong Chemical Reagent Company; Glacial acetic acid (AR grade), lot number: 201540201, expiration date: March 2020, specification: 500 ml/bottle, produced by Chengdu Kelong Chemical Reagent Company; Formaldehyde (AR grade), lot number: 2014120801, expiration date: November 2016, specification: 500 ml/bottle, produced by Chengdu Kelong Chemical Reagent Company. Preparation method: 4200 ml of 95% ethanol, 500 ml of formaldehyde, 300 ml of glacial acetic acid and 900 ml of purified water were weighed out and poured into a plastic barrel for fully uniform mixing to prepare FAA solution.

Dehydration Reagent:

absolute ethyl alcohol (AR grade), lot number: 2015052501, expiration date: April 2020, specification: 20 kg/barrel, by Chengdu Kelong Chemical Reagent Company. Preparation method: absolute ethyl alcohol is diluted with purified water to prepare 70%, 80% and 90% ethanol solution.

Transparent Reagent:

xylene (AR grade), lot number: 2014071001, expiration date: June 2019, specification: 500 ml/bottle, produced by Chengdu Kelong Chemical Reagent Company.

Hematoxylin Staining Solution:

Hematoxylin (AR grade), lot number: 2014010701, expiration date: April 2017, specification: 5 g/bottle, by Chengdu Kelong Chemical Reagent Company; Aluminum potassium sulfate (AR grade), lot number: 2014091601, expiration date: January 2017, specification: 500 g/bottle, by Chengdu Kelong Chemical Reagent Company; Sodium iodate (AR grade), lot number: 20140711, expiration date: January 2017, specification: 100 g/bottle, by Chengdu Kelong Chemical Reagent Company. Glycerol (AR grade), lot number: 2014122401, expiration date: December 2017, by Chengdu Kelong Chemical Reagent Company; Glacial acetic acid (AR grade), lot number: 201540201, expiration date: March 2020, specification: 500 ml/bottle, by Chengdu Kelong Chemical Reagent Company.

Preparation method: weighing 1.5002 g of hematoxylin and putting it into a beaker; adding 250 ml of purified water into the beaker, stirring until the hematoxylin fully dissolved; adding 312.5 ml of purified water and 0.3003 g of sodium iodate into the beaker, stirring for 5 minutes; adding 37.5004 g of aluminum potassium sulfate into the beaker until fully dissolved; and adding 187.5 ml of glycerol into the beaker for uniformly mixing; finally adding 7.5 ml of glacial acetic acid into the beaker until fully stirring and mixing to prepare hematoxylin staining solution.

Eosin Staining Solution:

Eosin (water soluble), lot number: 2013110501, expiration date: May 2016, specification: 25 g/bottle, by Chengdu Kelong Chemical Reagent Company; Absolute ethyl alcohol (AR grade), lot number: 2015052501, expiration date: April 2020, specification: 20 kg/barrel, by Chengdu Kelong Chemical Reagent Company.

Preparation method: weighing 600 ml of absolute ethyl alcohol and 150 ml of purified water in a beaker until uniformly mixing; and adding 3.7505 g of eosin into the beaker for uniformly stirring to prepare Eosin staining solution.

Hydrochloric Acid-Ethanol Differentiation Solution:

hydrochloric acid (AR grade), lot number: 2014072301, expiration date: Jul. 22, 2019, specification: 500 ml/bottle, by Chengdu Kelong Chemical Reagent Company; Absolute ethyl alcohol (AR grade), lot number: 2015052501, expiration date: April 2020, specification: 20 kg/barrel, by Chengdu Kelong Chemical Reagent Company.

Preparation method: adding 520 ml of absolute ethyl alcohol and 222.5 ml of purified water into a beaker, uniformly mixing; and slowly adding 7.5 ml of concentrated hydrochloric acid, stirring and uniformly mixing, to prepare hydrochloric acid-ethanol differentiation solution.

Sealing Reagent:

Neutral resin, lot number: 20140106, expiration date: December 2018, specification: 100 g/bottle, by Shanghai Yiyang instruments Co., Ltd., China.

Cover Clip Cleaning Solution:

Potassium dichromate (AR grade), lot number: 20120822, expiration date: July 2016, specification: 500 g/bottle, by Chengdu Kelong Chemical Reagent Company; Concentrated sulfuric acid (AR grade), lot number: 2014072301, 20130607, expiration date: Jul. 22, 2019, Jun. 6, 2018, specification: 500 ml/bottle, by Chengdu Kelong Chemical Reagent Company.

Preparation method: adding 500 ml of purified water and 50.0003 g of potassium dichromate into a beaker for stirring, dissolving and uniformly mixing; and slowly adding 50 ml of concentrated sulfuric acid until uniformly mixing to prepare cover clip cleaning solution.

2.4 Model Establishment

After quarantine and adaptability observation, 392 qualified Japanese white rabbits were obtained, with the weight of 2.070-2.560 kg, all male. Eight were taken as control group and the rest were treated by a striking device. Striking area was a round surface with the diameter of 1.5 cm, the wounding energy was calculated according to Ep=mgh, and the energy of each striking of the iron rod is 7.5 J.

Specifically: the rabbit was anesthetized by intravenous injection of 3% pentobarbital sodium at ear edge with the dose of 1 ml/kg. The rabbit was kept laying down at right side prostrate position and the left thigh was set on the striking platform. Found the trochanter of the left femur and set the striking head attached to area from the trochanter to the 1.5 cm below. The self-made striking device was used for striking the outer side of the thigh near-end, and the plaster was used for fixing the left limb on the hip/knee-bending area. When the plaster bandage was applied and the right hip was examined to move freely, the rabbit was kept to lay down until solidification. After the model establishment, the animal was allowed to drink water normally and was fed with granular food. No anticoagulant or antibiotic was used.

2.5 Grouping and Drug Administration 2.5.1 Drug Preparation

The mixture of Drug (mg):Carboxymethylcellulose (mg): lactose (mg):mannitol (mg)=1:2:10:20, was uniformly grinded, then 1 ml of purified water was added into the mixture, stirring until uniform for use. Embodiment: the mixture of 50 mg drug+100 mg carboxymethylcellulose+ 500 mg lactose+1000 mg mannitol, was uniformly grinded, then 50 ml of water was added into the mixture, uniformly stirring to obtain 1 mg/ml solution.

2.5.2 Drug Delivery

Animals were grouped after modeling. The drug was fed according to table 4 via oral gavage, once a day for 7 days continuously.

TABLE 4

Drug administration plan

| Group | Administration route | Administrated subject | Dosage (mg/kg) | Dosing frequency |
|---|---|---|---|---|
| Control | i.g | auxiliary | — | — |
| Model | i.g | auxiliary | — | — |
| Ginkgolide B | i.g | Ginkgolide B | 5 | 1 |
| Rivaroxaban | i.g | Rivaroxaban | 5 | 1 |
| Apixaban | i.g | Apixaban | 5 | 1 |
| Edoxaban | i.g | Edoxaban | 5 | 1 |
| Razaxaban | i.g | Razaxaban | 5 | 1 |
| Otamixaban | i.g | Otamixaban | 5 | 1 |
| Composition 1 | i.g | Composition 1 | 5 | 1 |
| Composition 2 | i.g | Composition 2 | 5 | 1 |
| Composition 3 | i.g | Composition 3 | 5 | 1 |
| Composition 4 | i.g | Composition 4 | 5 | 1 |
| Composition 5 | i.g | Composition 5 | 5 | 1 |
| Composition 6 | i.g | Composition 6 | 5 | 1 |
| Composition 7 | i.g | Composition 7 | 5 | 1 |
| Composition 8 | i.g | Composition 8 | 5 | 1 |
| Composition 9 | i.g | Composition 9 | 5 | 1 |
| Composition 10 | i.g | Composition 10 | 5 | 1 |
| Composition 11 | i.g | Composition 11 | 5 | 1 |
| Composition 12 | i.g | Composition 12 | 5 | 1 |
| Composition 13 | i.g | Composition 13 | 5 | 1 |
| Composition 14 | i.g | Composition 14 | 5 | 1 |
| Composition 15 | i.g | Composition 15 | 5 | 1 |
| Composition 16 | i.g | Composition 16 | 5 | 1 |
| Composition 17 | i.g | Composition 17 | 5 | 1 |
| Composition 18 | i.g | Composition 18 | 5 | 1 |
| Composition 19 | i.g | Composition 19 | 5 | 1 |
| Composition 20 | i.g | Composition 20 | 5 | 1 |
| Composition 21 | i.g | Composition 21 | 5 | 1 |
| Composition 22 | i.g | Composition 22 | 5 | 1 |
| Composition 23 | i.g | Composition 23 | 5 | 1 |
| Composition 24 | i.g | Composition 24 | 5 | 1 |
| Composition 25 | i.g | Composition 25 | 5 | 1 |
| Composition 26 | i.g | Composition 26 | 5 | 1 |
| Composition 27 | i.g | Composition 27 | 5 | 1 |
| Composition 28 | i.g | Composition 28 | 5 | 1 |
| Composition 29 | i.g | Composition 29 | 5 | 1 |
| Composition 30 | i.g | Composition 30 | 5 | 1 |
| Composition 31 | i.g | Composition 31 | 5 | 1 |
| Composition 32 | i.g | Composition 32 | 5 | 1 |
| Composition 33 | i.g | Composition 33 | 5 | 1 |
| Composition 34 | i.g | Composition 34 | 5 | 1 |
| Composition 35 | i.g | Composition 35 | 5 | 1 |
| Composition 36 | i.g | Composition 36 | 5 | 1 |
| Composition 37 | i.g | Composition 37 | 5 | 1 |
| Composition 38 | i.g | Composition 38 | 5 | 1 |
| Composition 39 | i.g | Composition 39 | 5 | 1 |
| Composition 40 | i.g | Composition 40 | 5 | 1 |
| Composition 41 | i.g | Composition 41 | 5 | 1 |

2.6 Detection 2.6.1 Coagulation Function and Coagulation Factor Activity Detection At 0.5, 1.0, 2.0, 3.0 and 4.0 h after the first administration, blood was taken from ear central artery. Plasma was separated and aPPT, PT and the anti-factor Xa activity were determined on an automatic coagulation detector.

2.6.2 PAF Content Change

At 0.5, 1.0, 2.0, 3.0 and 4.0 h after the first administration, blood was taken from ear central artery. Plasma was separated and the content of PAF was determined by ELISA.

2.6.3 Deep Venous Thrombosis Forming Test 30 mins after the last administration, the animal was euthanized. Femoral arteries and venous were collected, HE stained, and inspected through a microscope for the vascular endothelial injury, thrombosis and blood vessel fracture. All phenotype were graded. Grading standard is showed in Table 5.

TABLE 5

Grading standard of pathohistological changes of deep venous thrombosis

| | | Examination and standard | Pathological grading | Grading (points) |
|---|---|---|---|---|
| Blood vesicle | Endothelium damage | Intact endothelium, no abnormality | (−) | 0 |
| | | Endothelial cells swelling and degeneration | (+) | 1 |
| | | Endothelial cells necrosis and falling, reducing number | (++) | 2 |
| | | Endothelial cells necrosis and falling, loss Endothelium | (+++) | 3 |
| | Thrombus formation | No thrombus | (−) | 0 |
| | | Thrombus <1/3 of blood vesicle diameter | (+) | 1 |
| | | Thrombus is larger than 1/3 but less than 2/3 of blood vesicle diameter | (++) | 2 |
| | | Size of thrombosis >2/3 of blood vesicle diameter, or block the vesicle | (+++) | 3 |
| | Broken blood vesicle | Intact vesicular wall, no abnormality | (−) | 0 |
| | | Broken vesicular wall, hematopoietic cells infiltration | (+++) | 3 |

2.7 Statistical Analysis

Coagulation function, coagulation factor and PAF content data were analyzed. Excel was adopted to calculate the average and the standard deviation, and to determine whether the data was normalized. If the data was normalized, F test in the Excel was adopted to test the variance of deviation. Otherwise, perform the non-parameter test.

The pathological test data was graded data and was analyzed by using SPSS 13.0 through non-parameter test of multiple independent samples.

3. Experiment Results 3.1 Coagulation Function and Anti-Coagulation Factor Activity

TABLE 6

Result of aPPT of coagulation function ($\bar{x} \pm SD$, s)

| Group | 0.5 h after administration | 1 h after administration | 2 h after administration | 3 h after administration | 4 h after administration |
|---|---|---|---|---|---|
| Control | 29.53 ± 8.77 | 26.31 ± 9.53 | 30.27 ± 7.29 | 24.06 ± 8.92 | 24.82 ± 9.29 |
| Model | 24.70 ± 5.90 | 22.91 ± 5.57 | 32.69 ± 7.27 | 26.79 ± 10.06 | 29.79 ± 7.51 |
| Ginkgolide B | 25.89 ± 8.15 | 30.65 ± 6.79* | 25.83 ± 5.96 | 34.30 ± 6.56 | 31.92 ± 7.77 |
| Rivaroxaban | 27.89 ± 7.97 | 32.01 ± 9.31* | 34.63 ± 5.57 | 35.92 ± 10.85 | 29.20 ± 6.32 |
| Apixaban | 19.05 ± 6.17 | 24.26 ± 7.89 | 23.94 ± 5.49 | 31.71 ± 8.53 | 29.21 ± 11.35 |
| Edoxaban | 26.77 ± 7.65 | 25.01 ± 9.52 | 33.63 ± 5.45 | 36.47 ± 9.12 | 27.20 ± 6.31 |
| Razaxaban | 20.13 ± 6.74 | 26.23 ± 8.43 | 22.33 ± 4.46 | 35.75 ± 8.68 | 29.65 ± 9.72 |
| Otamixaban | 21.67 ± 9.42 | 25.71 ± 7.68 | 25.61 ± 6.75 | 34.62 ± 7.59 | 30.16 ± 9.37 |
| Composition 1 | 29.21 ± 9.08 | 36.44 ± 7.66** | 24.48 ± 8.23* | 30.53 ± 6.77 | 32.92 ± 4.64 |
| Composition 2 | 28.64 ± 6.54 | 32.66 ± 8.59* | 35.24 ± 4.34 | 36.99 ± 7.65 | 30.90 ± 8.15 |
| Composition 3 | 25.64 ± 3.41 | 33.75 ± 8.16** | 31.29 ± 4.96 | 30.89 ± 6.40 | 33.90 ± 8.02 |
| Composition 4 | 25.77 ± 6.85 | 30.69 ± 8.36 | 36.63 ± 5.64 | 36.46 ± 9.31 | 31.20 ± 6.52 |
| Composition 5 | 19.13 ± 6.56 | 34.23 ± 9.46** | 35.33 ± 4.45 | 30.74 ± 7.68 | 30.65 ± 7.65 |
| Composition 6 | 20.36 ± 9.14 | 32.71 ± 7.66* | 35.61 ± 6.78 | 36.62 ± 7.57 | 32.16 ± 8.67 |
| Composition 7 | 21.36 ± 7.69 | 34.63 ± 7.91** | 35.45 ± 6.75 | 31.52 ± 6.84 | 32.61 ± 8.27 |
| Composition 8 | 20.94 ± 5.84 | 35.64 ± 8.75** | 36.14 ± 8.17 | 31.67 ± 9.17 | 31.67 ± 8.19 |
| Composition 9 | 29.71 ± 8.42 | 35.54 ± 12.24** | 25.93 ± 5.93* | 30.25 ± 6.04 | 33.23 ± 4.18 |
| Composition 10 | 32.77 ± 7.24 | 29.06 ± 7.22* | 36.65 ± 15.54 | 29.52 ± 7.39 | 28.76 ± 5.68 |
| Composition 11 | 27.70 ± 9.07 | 31.37 ± 9.86* | 29.62 ± 9.51 | 28.88 ± 5.37 | 29.54 ± 5.92 |
| Composition 12 | 28.67 ± 8.14 | 33.71 ± 7.48* | 35.47 ± 6.75 | 34.62 ± 7.54 | 33.14 ± 8.98 |
| Composition 13 | 25.16 ± 6.75 | 35.25 ± 9.95** | 35.74 ± 5.67 | 31.64 ± 7.75 | 31.64 ± 7.57 |
| Composition 14 | 20.78 ± 9.48 | 34.71 ± 7.74** | 35.49 ± 6.95 | 36.76 ± 7.84 | 32.96 ± 8.74 |
| Composition 15 | 21.55 ± 7.89 | 34.59 ± 7.76** | 35.44 ± 6.79 | 31.39 ± 6.69 | 32.88 ± 8.97 |
| Composition 16 | 20.64 ± 5.77 | 35.89 ± 8.55** | 36.75 ± 8.66 | 31.84 ± 9.48 | 31.84 ± 8.96 |
| Composition 17 | 29.30 ± 8.54 | 35.80 ± 12.36** | 25.45 ± 7.69* | 30.28 ± 6.64 | 33.75 ± 4.95 |
| Composition 18 | 32.82 ± 7.69 | 29.57 ± 7.99* | 36.56 ± 15.78 | 29.94 ± 7.56 | 28.84 ± 5.59 |
| Composition 19 | 27.91 ± 9.26 | 31.76 ± 9.94* | 29.58 ± 9.74 | 28.67 ± 5.95 | 29.57 ± 5.64 |
| Composition 20 | 33.65 ± 7.85 | 33.46 ± 7.87* | 36.48 ± 15.95 | 29.75 ± 7.48 | 28.75 ± 5.83 |
| Composition 21 | 34.81 ± 7.75 | 33.68 ± 7.82* | 36.94 ± 15.59 | 29.65 ± 7.44 | 28.76 ± 5.89 |
| Composition 22 | 27.55 ± 7.16 | 36.47 ± 7.56** | 35.26 ± 6.49 | 31.69 ± 6.72 | 32.73 ± 8.18 |
| Composition 23 | 26.64 ± 5.29 | 35.99 ± 8.48** | 36.64 ± 8.72 | 31.43 ± 9.55 | 31.95 ± 8.64 |
| Composition 24 | 23.46 ± 7.85 | 36.75 ± 7.82** | 35.48 ± 6.80 | 31.19 ± 6.48 | 32.15 ± 8.73 |
| Composition 25 | 29.25 ± 8.78 | 35.65 ± 12.85** | 25.56 ± 5.64* | 30.85 ± 6.96 | 33.49 ± 8.62 |
| Composition 26 | 30.67 ± 7.00 | 33.52 ± 7.96* | 36.56 ± 15.26 | 29.35 ± 7.84 | 28.62 ± 5.85 |
| Composition 27 | 29.81 ± 7.17 | 33.64 ± 7.45* | 36.44 ± 10.64 | 29.46 ± 7.52 | 28.43 ± 5.42 |
| Composition 28 | 27.48 ± 5.96 | 36.72 ± 7.63** | 35.58 ± 6.64 | 31.28 ± 6.65 | 32.45 ± 8.55 |
| Composition 29 | 26.77 ± 5.55 | 35.58 ± 8.23** | 36.66 ± 8.75 | 31.44 ± 9.28 | 31.63 ± 8.45 |
| Composition 30 | 28.30 ± 8.46 | 35.75 ± 10.64** | 24.26 ± 6.37* | 30.58 ± 6.57 | 33.56 ± 5.00 |
| Composition 31 | 32.42 ± 7.22 | 31.69 ± 7.41* | 36.23 ± 9.47 | 29.56 ± 7.47 | 28.98 ± 5.36 |
| Composition 32 | 27.68 ± 9.48 | 31.28 ± 9.36* | 29.59 ± 9.82 | 28.63 ± 5.41 | 29.45 ± 5.69 |
| Composition 33 | 33.55 ± 7.96 | 34.36 ± 7.85** | 36.96 ± 15.23 | 29.71 ± 7.23 | 28.69 ± 5.64 |
| Composition 34 | 34.96 ± 7.12 | 33.23 ± 7.55* | 36.64 ± 15.38 | 29.45 ± 7.26 | 28.82 ± 5.38 |
| Composition 35 | 30.65 ± 9.22 | 32.65 ± 9.64* | 30.69 ± 9.47 | 28.96 ± 5.57 | 30.64 ± 8.39 |
| Composition 36 | 30.68 ± 8.65 | 32.68 ± 8.25* | 35.68 ± 8.64 | 29.58 ± 7.84 | 28.58 ± 5.28 |

TABLE 6-continued

Result of aPPT of coagulation function ($\bar{x} \pm SD$, s)

| Group | 0.5 h after administration | 1 h after administration | 2 h after administration | 3 h after administration | 4 h after administration |
|---|---|---|---|---|---|
| Composition 37 | 31.47 ± 5.94 | 33.75 ± 7.11* | 36.14 ± 15.16 | 29.29 ± 7.96 | 28.85 ± 5.55 |
| Composition 38 | 27.85 ± 7.96 | 36.44 ± 7.77** | 35.95 ± 6.05 | 31.39 ± 6.41 | 32.65 ± 8.45 |
| Composition 39 | 26.72 ± 5.58 | 35.83 ± 8.64** | 36.74 ± 8.49 | 31.57 ± 9.68 | 31.82 ± 8.63 |
| Composition 40 | 23.82 ± 7.34 | 36.91 ± 7.50** | 35.53 ± 6.67 | 31.58 ± 6.65 | 32.42 ± 8.95 |
| Composition 41 | 29.74 ± 8.45 | 36.64 ± 12.27** | 30.58 ± 8.27 | 30.52 ± 5.86 | 34.16 ± 8.51 |

1) Model group vs control group $p > 0.05$,
2) Model group vs drug group *$p < 0.05$ **$p < 0.01$ From table 6: 1) 0.5 h-4 h after administration, comparing the aPTT (activated partial thromboplastin time) of model group with the control group, no obvious extension was observed (p>0.05), indicating the success of the modeling. 2) 0.5 h-4 h after administration, comparing the aPTT of the model group with the groups administrated with medicine, no obvious extension was observed (p>0.05), indicating Ginkgolide B, xaban and compositions did not result bleeding adverse effect. 3) 1 h after administration, comparing the aPTT of the model group, the aPTT of the Ginkgolide B and Rivaroxaban group were obviously extended (p<0.05) and no obvious extension was observed (p>0.05) for Apixaban, Edoxaban, Razaxaban and Otamixaban groups; the aPTT of Ginkgolide B+xaban groups were significantly extended (p<0.01) and obviously extended (p<0.05), indicating the pharmaceutical composition of the present invention can effectively extend aPPT and the Ginkgolide B and xaban work synergistically on the extention of aPPT.

TABLE 7

Result of PT of coagulation function ($\bar{x} \pm SD$, s)

| Group | 0.5 h after administration | 1 h after administration | 2 h after administration | 3 h after administration | 4 h after administration |
|---|---|---|---|---|---|
| Control | 6.83 ± 0.31 | 6.89 ± 0.39 | 6.83 ± 0.17 | 6.83 ± 0.30 | 6.78 ± 0.23 |
| Model | 6.59 ± 0.23 | 6.69 ± 0.26 | 7.07 ± 1.47 | 6.66 ± 0.22 | 6.73 ± 0.16 |
| Ginkgolide B | 6.76 ± 0.32 | 6.79 ± 0.27 | 6.75 ± 0.36 | 6.72 ± 0.24 | 6.68 ± 0.23 |
| Rivaroxaban | 6.76 ± 0.30 | 7.20 ± 0.96 | 6.90 ± 0.24 | 6.81 ± 0.22 | 6.70 ± 0.33 |
| Apixaban | 6.78 ± 0.21 | 6.76 ± 0.21 | 6.70 ± 0.19 | 6.70 ± 0.24 | 7.14 ± 0.87 |
| Edoxaban | 6.73 ± 0.15 | 6.14 ± 0.26 | 6.28 ± 0.42 | 6.45 ± 0.65 | 6.42 ± 0.34 |
| Razaxaban | 6.71 ± 0.25 | 7.41 ± 0.51 | 6.47 ± 0.25 | 6.47 ± 0.41 | 6.70 ± 0.25 |
| Otamixaban | 6.58 ± 0.45 | 6.74 ± 0.26 | 6.52 ± 0.43 | 6.62 ± 0.42 | 7.82 ± 0.31 |
| Composition 1 | 7.03 ± 0.13** | 6.56 ± 0.34 | 6.47 ± 0.34 | 6.58 ± 0.18 | 6.57 ± 0.16 |
| Composition 2 | 6.86 ± 0.21* | 6.73 ± 0.25 | 6.85 ± 0.30 | 6.70 ± 0.28 | 6.71 ± 0.28 |
| Composition 3 | 6.82 ± 0.22* | 6.83 ± 0.24 | 6.76 ± 0.20 | 6.84 ± 0.34 | 6.94 ± 0.24 |
| Composition 4 | 6.85 ± 0.34* | 6.56 ± 0.77 | 6.48 ± 0.56 | 6.75 ± 0.35 | 6.75 ± 0.26 |
| Composition 5 | 6.99 ± 0.32** | 6.46 ± 0.26 | 6.58 ± 0.25 | 6.74 ± 0.58 | 6.69 ± 0.28 |
| Composition 6 | 6.86 ± 0.24* | 6.74 ± 0.58 | 6.74 ± 0.34 | 6.81 ± 0.29 | 6.83 ± 0.50 |
| Composition 7 | 6.95 ± 0.26** | 6.79 ± 0.25 | 6.78 ± 0.38 | 6.79 ± 0.34 | 6.85 ± 0.19 |
| Composition 8 | 6.91 ± 0.41** | 6.78 ± 0.34 | 6.95 ± 0.18 | 6.84 ± 0.24 | 6.67 ± 0.26 |
| Composition 9 | 7.10 ± 0.23** | 6.86 ± 0.26 | 6.83 ± 0.28 | 6.97 ± 0.56 | 6.85 ± 0.35 |
| Composition 10 | 6.84 ± 0.29* | 6.88 ± 0.33 | 6.72 ± 0.15 | 6.75 ± 0.20 | 6.75 ± 0.30 |
| Composition 11 | 6.88 ± 0.12* | 6.97 ± 0.24 | 7.07 ± 1.18 | 7.06 ± 0.88 | 7.07 ± 0.54 |
| Composition 12 | 6.81 ± 0.19* | 6.83 ± 0.31 | 6.83 ± 0.13 | 6.89 ± 0.62 | 6.74 ± 0.13 |
| Composition 13 | 7.02 ± 0.33** | 6.80 ± 0.30 | 6.87 ± 0.15 | 6.68 ± 0.25 | 6.79 ± 0.28 |
| Composition 14 | 6.92 ± 0.24** | 6.64 ± 0.21 | 6.82 ± 0.34 | 6.79 ± 0.19 | 6.95 ± 0.30 |
| Composition 15 | 7.00 ± 0.18** | 6.92 ± 0.26 | 6.79 ± 0.17 | 6.83 ± 0.48 | 6.91 ± 0.24 |
| Composition 16 | 6.95 ± 0.23** | 6.95 ± 0.29 | 6.85 ± 0.36 | 6.58 ± 0.24 | 6.86 ± 0.28 |
| Composition 17 | 7.07 ± 0.52** | 6.58 ± 0.35 | 6.96 ± 0.41 | 6.85 ± 0.36 | 6.95 ± 0.26 |
| Composition 18 | 6.88 ± 0.22* | 6.93 ± 0.24 | 6.85 ± 0.25 | 6.92 ± 0.21 | 6.84 ± 0.28 |
| Composition 19 | 6.86 ± 0.31* | 6.68 ± 0.35 | 6.99 ± 0.95 | 7.00 ± 0.65 | 7.14 ± 0.35 |
| Composition 20 | 6.81 ± 0.25* | 6.79 ± 0.29 | 6.85 ± 0.26 | 6.79 ± 0.53 | 6.88 ± 0.26 |
| Composition 21 | 6.89 ± 0.27* | 6.95 ± 0.19 | 6.86 ± 0.28 | 6.93 ± 0.36 | 7.00 ± 0.31 |
| Composition 22 | 7.05 ± 0.25** | 6.85 ± 0.36 | 6.84 ± 0.28 | 6.86 ± 0.26 | 6.89 ± 0.19 |
| Composition 23 | 6.98 ± 0.26** | 6.87 ± 0.51 | 6.95 ± 0.15 | 6.79 ± 0.19 | 6.95 ± 0.29 |
| Composition 24 | 7.03 ± 0.29** | 6.98 ± 0.24 | 6.79 ± 0.17 | 6.86 ± 0.27 | 6.88 ± 0.35 |
| Composition 25 | 7.05 ± 0.45** | 6.74 ± 0.15 | 6.87 ± 0.35 | 6.92 ± 0.42 | 6.86 ± 0.46 |
| Composition 26 | 6.89 ± 0.19* | 6.82 ± 0.46 | 6.94 ± 0.47 | 6.98 ± 0.29 | 6.79 ± 0.18 |
| Composition 27 | 6.83 ± 0.24* | 6.75 ± 0.36 | 6.85 ± 0.74 | 6.85 ± 0.63 | 7.01 ± 0.15 |
| Composition 28 | 7.01 ± 0.18** | 6.69 ± 0.42 | 6.77 ± 0.52 | 6.95 ± 0.25 | 6.85 ± 0.26 |
| Composition 29 | 7.00 ± 0.31** | 6.78 ± 0.35 | 6.96 ± 0.24 | 6.97 ± 0.28 | 6.96 ± 0.27 |
| Composition 30 | 7.15 ± 0.27** | 6.86 ± 0.14 | 6.88 ± 0.29 | 6.95 ± 0.24 | 6.88 ± 0.17 |
| Composition 31 | 6.89 ± 0.16* | 6.88 ± 0.20 | 6.74 ± 0.23 | 6.99 ± 0.18 | 6.79 ± 0.35 |
| Composition 32 | 6.85 ± 0.24* | 6.95 ± 0.24 | 6.78 ± 0.56 | 6.97 ± 0.36 | 7.01 ± 0.26 |
| Composition 33 | 6.86 ± 0.19* | 7.01 ± 0.23 | 6.96 ± 0.42 | 6.76 ± 0.46 | 6.96 ± 0.18 |
| Composition 34 | 6.88 ± 0.34* | 6.76 ± 0.26 | 6.79 ± 0.34 | 6.85 ± 0.28 | 6.98 ± 0.24 |
| Composition 35 | 6.85 ± 0.22* | 6.65 ± 0.64 | 6.48 ± 0.96 | 7.03 ± 0.16 | 6.85 ± 0.42 |
| Composition 36 | 6.86 ± 0.60* | 6.98 ± 0.26 | 6.67 ± 0.51 | 6.95 ± 0.62 | 6.80 ± 0.23 |
| Composition 37 | 6.84 ± 0.63* | 6.85 ± 0.46 | 6.89 ± 0.41 | 6.95 ± 0.28 | 6.74 ± 0.52 |
| Composition 38 | 7.12 ± 0.26** | 6.96 ± 0.55 | 6.89 ± 0.45 | 6.78 ± 0.27 | 6.95 ± 0.35 |

TABLE 7-continued

Result of PT of coagulation function ($\bar{x} \pm SD$, s)

| Group | 0.5 h after administration | 1 h after administration | 2 h after administration | 3 h after administration | 4 h after administration |
|---|---|---|---|---|---|
| Composition 39 | 7.05 ± 0.65** | 6.99 ± 0.65 | 6.47 ± 0.74 | 6.86 ± 0.51 | 6.85 ± 0.37 |
| Composition 40 | 7.06 ± 0.29** | 6.75 ± 0.29 | 6.76 ± 0.42 | 6.83 ± 0.36 | 6.96 ± 0.28 |
| Composition 41 | 6.98 ± 0.52** | 6.86 ± 0.25 | 6.68 ± 0.36 | 6.86 ± 0.85 | 6.96 ± 0.26 |

1) Model group vs control group p > 0.05,
2) Model group vs drug group *p < 0.05

From table 7: 1) 0.5 h-4 h after administration, comparing the PT (prothrombin time) of model group with the control group, no obvious extension was observed (p>0.05), indicating the success of the modeling. 2) 0.5 h-4 h after administration, comparing the PT of the model group with the groups administrated with medicine, no obvious extension was observed (p>0.05), indicating Ginkgolide B, xaban and compositions did not result bleeding adverse effect. 3) 0.5 h after administration, comparing the PT (prothrombin time) of the model group, the PT of each composition group was obviously extended (p<0.05) and significantly extended (p<0.01), indicating the pharmaceutical composition of the present invention can effectively extend PT and the Ginkgolide B and xaban work synergistically on the extention of PT.

TABLE 8

Result of anti-factor Xa activity ($\bar{x} \pm SD$, IU/ml)

| Group | 0.5 h after administration | 1 h after administration | 2 h after administration | 3 h after administration | 4 h after administration |
|---|---|---|---|---|---|
| Control | 0.10 ± 0.05 | 0.10 ± 0.05 | 0.10 ± 0.06 | 0.09 ± 0.08 | 0.09 ± 0.06 |
| Model | 0.09 ± 0.07 | 0.08 ± 0.05 | 0.13 ± 0.06 | 0.09 ± 0.09 | 0.13 ± 0.07 |
| Ginkgolide B | 0.08 ± 0.07 | 0.10 ± 0.10 | 0.35 ± 0.22* | 0.74 ± 0.15*** | 0.65 ± 0.12*** |
| Rivaroxaban | 0.37 ± 0.09*** | 0.31 ± 0.13*** | 0.18 ± 0.05* | 1.32 ± 0.16*** | 1.38 ± 0.18*** |
| Apixaban | 0.16 ± 0.10*** | 0.26 ± 0.04*** | 0.25 ± 0.10* | 1.22 ± 0.22*** | 1.12 ± 0.15*** |
| Edoxaban | 0.25 ± 0.06*** | 0.21 ± 0.08*** | 0.20 ± 0.10* | 1.26 ± 0.09*** | 1.26 ± 0.07*** |
| Razaxaban | 0.20 ± 0.14*** | 0.18 ± 0.05*** | 0.23 ± 0.08* | 1.31 ± 0.30*** | 1.32 ± 0.09*** |
| Otamixaban | 0.19 ± 0.04*** | 0.25 ± 0.10*** | 0.26 ± 0.10* | 1.25 ± 0.12*** | 1.24 ± 0.06*** |
| Composition 1 | 0.41 ± 0.18*** | 0.17 ± 0.03*** | 0.94 ± 0.13*** | 1.37 ± 0.32*** | 1.15 ± 0.16*** |
| Composition 2 | 0.32 ± 0.05*** | 0.31 ± 0.13*** | 1.10 ± 0.19*** | 1.27 ± 0.22*** | 1.06 ± 0.21*** |
| Composition 3 | 0.30 ± 0.07*** | 0.25 ± 0.07*** | 1.20 ± 0.10*** | 1.28 ± 0.10*** | 1.30 ± 0.09*** |
| Composition 4 | 0.24 ± 0.12*** | 0.30 ± 0.05*** | 1.23 ± 0.08*** | 1.23 ± 0.52*** | 1.42 ± 0.05*** |
| Composition 5 | 0.20 ± 0.06*** | 0.36 ± 0.13*** | 1.26 ± 0.14*** | 1.30 ± 0.12*** | 1.26 ± 0.08*** |
| Composition 6 | 0.35 ± 0.25*** | 0.34 ± 0.05*** | 1.34 ± 0.13*** | 1.34 ± 0.42*** | 1.20 ± 0.30*** |
| Composition 7 | 0.34 ± 0.09*** | 0.29 ± 0.08*** | 1.22 ± 0.23*** | 1.35 ± 0.32*** | 1.28 ± 0.40*** |
| Composition 8 | 0.40 ± 0.08*** | 0.32 ± 0.12*** | 1.41 ± 0.04*** | 1.28 ± 0.29*** | 1.34 ± 0.36*** |
| Composition 9 | 0.46 ± 0.04*** | 0.24 ± 0.21*** | 1.03 ± 0.21*** | 1.30 ± 0.18*** | 1.26 ± 0.31*** |
| Composition 10 | 0.32 ± 0.08*** | 0.25 ± 0.12*** | 0.74 ± 0.17*** | 1.16 ± 0.12*** | 0.70 ± 0.16*** |
| Composition 11 | 0.25 ± 0.05*** | 0.29 ± 0.17*** | 1.21 ± 0.06*** | 1.31 ± 0.15*** | 1.12 ± 0.07*** |
| Composition 12 | 0.26 ± 0.04*** | 0.32 ± 0.21*** | 0.95 ± 0.23*** | 0.96 ± 0.20*** | 1.05 ± 0.15*** |
| Composition 13 | 0.45 ± 0.09*** | 0.35 ± 0.20*** | 1.05 ± 0.22*** | 1.21 ± 0.11*** | 1.09 ± 0.15*** |
| Composition 14 | 0.35 ± 0.08*** | 0.32 ± 0.17*** | 1.14 ± 0.08*** | 1.20 ± 0.09*** | 1.06 ± 0.08*** |
| Composition 15 | 0.43 ± 0.03*** | 0.30 ± 0.14*** | 1.35 ± 0.25*** | 1.34 ± 0.19*** | 1.12 ± 0.24*** |
| Composition 16 | 0.40 ± 0.10*** | 0.32 ± 0.15*** | 1.54 ± 0.20*** | 1.26 ± 0.31*** | 1.34 ± 0.20*** |
| Composition 17 | 0.50 ± 0.04*** | 0.32 ± 0.06*** | 1.35 ± 0.09*** | 1.29 ± 0.09*** | 1.26 ± 0.08*** |
| Composition 18 | 0.30 ± 0.06*** | 0.35 ± 0.24*** | 1.24 ± 0.16*** | 1.28 ± 0.06*** | 1.21 ± 0.23*** |
| Composition 19 | 0.33 ± 0.08*** | 0.31 ± 0.20*** | 1.15 ± 0.36*** | 1.41 ± 0.25*** | 1.19 ± 0.35*** |
| Composition 20 | 0.31 ± 0.03*** | 0.29 ± 0.16*** | 1.09 ± 0.06*** | 1.24 ± 0.04*** | 1.14 ± 0.05*** |
| Composition 21 | 0.36 ± 0.07*** | 0.36 ± 0.12*** | 1.29 ± 0.08*** | 1.29 ± 0.05*** | 1.06 ± 0.06*** |
| Composition 22 | 0.46 ± 0.06*** | 0.39 ± 0.06*** | 1.46 ± 0.19*** | 1.42 ± 0.26*** | 1.46 ± 0.18*** |
| Composition 23 | 0.37 ± 0.09*** | 0.35 ± 0.32*** | 1.31 ± 0.09*** | 1.32 ± 0.07*** | 1.41 ± 0.09*** |
| Composition 24 | 0.42 ± 0.07*** | 0.40 ± 0.07*** | 1.25 ± 0.07*** | 1.26 ± 0.08*** | 1.28 ± 0.06*** |
| Composition 25 | 0.45 ± 0.08*** | 0.30 ± 0.08*** | 1.12 ± 0.15*** | 1.35 ± 0.06*** | 1.25 ± 0.09*** |
| Composition 26 | 0.34 ± 0.06*** | 0.34 ± 0.05*** | 1.21 ± 0.08*** | 1.29 ± 0.08*** | 1.41 ± 0.09*** |
| Composition 27 | 0.35 ± 0.09*** | 0.40 ± 0.08*** | 1.35 ± 0.09*** | 1.32 ± 0.06*** | 1.32 ± 0.27*** |
| Composition 28 | 0.43 ± 0.07*** | 0.31 ± 0.30*** | 1.36 ± 0.02*** | 1.28 ± 0.01*** | 1.38 ± 0.05*** |
| Composition 29 | 0.42 ± 0.07*** | 0.40 ± 0.07*** | 1.25 ± 0.07*** | 1.26 ± 0.08*** | 1.28 ± 0.06*** |
| Composition 30 | 0.47 ± 0.08*** | 0.28 ± 0.26*** | 1.29 ± 0.05*** | 1.24 ± 0.06*** | 1.39 ± 0.05*** |
| Composition 31 | 0.36 ± 0.04*** | 0.38 ± 0.06*** | 1.36 ± 0.08*** | 1.39 ± 0.02*** | 1.35 ± 0.07*** |
| Composition 32 | 0.34 ± 0.03*** | 0.28 ± 0.04*** | 1.25 ± 0.09*** | 1.41 ± 0.08*** | 1.28 ± 0.04*** |
| Composition 33 | 0.31 ± 0.05*** | 0.36 ± 0.09*** | 1.29 ± 0.06*** | 1.30 ± 0.06*** | 1.31 ± 0.07*** |
| Composition 34 | 0.34 ± 0.01*** | 0.29 ± 0.06*** | 1.32 ± 0.10*** | 1.36 ± 0.08*** | 1.29 ± 0.05*** |
| Composition 35 | 0.36 ± 0.09*** | 0.27 ± 0.26*** | 1.42 ± 0.01*** | 1.32 ± 0.05*** | 1.28 ± 0.06*** |
| Composition 36 | 0.37 ± 0.05*** | 0.35 ± 0.06*** | 1.38 ± 0.13*** | 1.29 ± 0.04*** | 1.34 ± 0.07*** |
| Composition 37 | 0.30 ± 0.06*** | 0.36 ± 0.08*** | 1.35 ± 0.07*** | 1.32 ± 0.07*** | 1.32 ± 0.09*** |
| Composition 38 | 0.45 ± 0.06*** | 0.31 ± 0.05*** | 1.32 ± 0.04*** | 1.36 ± 0.09*** | 1.28 ± 0.08*** |

TABLE 8-continued

Result of anti-factor Xa activity ($\bar{x} \pm SD$, IU/ml)

| Group | 0.5 h after administration | 1 h after administration | 2 h after administration | 3 h after administration | 4 h after administration |
|---|---|---|---|---|---|
| Composition 39 | 0.44 ± 0.08*** | 0.34 ± 0.06*** | 1.37 ± 0.09*** | 1.39 ± 0.06*** | 1.35 ± 0.08*** |
| Composition 40 | 0.44 ± 0.10*** | 0.35 ± 0.25*** | 1.38 ± 0.06*** | 1.41 ± 0.04*** | 1.37 ± 0.02*** |
| Composition 41 | 0.40 ± 0.07*** | 0.29 ± 0.08*** | 1.41 ± 0.07*** | 1.38 ± 0.09*** | 1.28 ± 0.08*** |

1) Model group vs control group p > 0.05,
2) Model group vs drug group *p < 0.05 p < 0.01 *p < 0.001

Note: An effective anticoagulation is defined as plasma anti-factor Xa activity≥0.5 IU/ML (reported by "The use of low-molecular-weight heparin on patients with cardiovascular disease should be standlized", according to the pharmacokinetic of LMWH in vivo.)

From table 8: 1) 0.5 h-4 h after administration, comparing the anti-factor Xa activity of model group with the control group, no abnormality was observed (p>0.05), indicating the success of the modeling. 2) 0.5 h-4 h after administration, the anti-factor Xa activity of the Ginkgolide B increased with time (p<0.001), and the Rivaroxaban group and Apixaban group had extremely significant difference (p<0.001), indicating the anti-factor Xa activity of the xaban type drug was greater than the Ginkgolide B. 3) 2 h after administration, compared with the anti-factor Xa activity of the model group, the activity of groups administrated with single medicine was obviously increased (p<0.05), and the activity of groups administrated with compositions had extremely significant increase (p<0.001), indicating the pharmaceutical composition of the present invention can effectively increase the anti-factor Xa activity and the Ginkgolide B and xaban work synergistically on the anti-factor Xa activity.

3.2 Differences of Content of PAF

TABLE 9

Result of PAF content ($\bar{x} \pm SD$, ng/L)

| Group | 0.5 h after administration | 1 h after administration | 2 h after administration | 3 h after administration | 4 h after administration |
|---|---|---|---|---|---|
| Control | 965.71 ± 245.32 | 1275.71 ± 120.47 | 1291.43 ± 73.60 | 1749.29 ± 172.16 | 1391.43 ± 209.09 |
| Model | 1116.43 ± 125.99 | 1403.57 ± 307.82 | 1340.71 ± 274.51 | 1985.00 ± 1007.73 | 1702.86 ± 448.96 |
| Ginkgolide B | 850.71* ± 284.79 | 1255.71 ± 300.73 | 975.71** ± 146.46 | 1656.43 ± 259.36 | 1155.00* ± 414.16 |
| Rivaroxaban | 886.43 ± 314.24 | 1484.29 ± 129.00 | 1061.43* ± 276.83 | 1671.43 ± 236.95 | 862.86*** ± 261.14 |
| Apixaban | 876.64* ± 226.44 | 1543.57 ± 239.95 | 1117.86 ± 231.52 | 1865.71 ± 371.23 | 879.29*** ± 316.20 |
| Edoxaban | 823.73* ± 277.74 | 1236.72 ± 301.62 | 1000.71* ± 125.46 | 1623.43 ± 256.35 | 1174.26* ± 423.11 |
| Razaxaban | 889.42 ± 326.32 | 1501.29 ± 131.10 | 1032.26* ± 312.11 | 1641.26 ± 242.32 | 932.86** ± 252.24 |
| Otamixaban | 845.54* ± 236.14 | 1526.56 ± 212.31 | 1123.45 ± 224.51 | 1745.52 ± 356.26 | 993.21** ± 235.25 |
| Composition 1 | 772.86** ± 373.24 | 1553.57** ± 222.81 | 1895.71*** ± 188.25 | 2385.71 ± 429.70 | 682.14*** ± 172.50 |
| Composition 2 | 784.45** ± 326.35 | 1525.65** ± 241.21 | 1865.25*** ± 174.32 | 2377.71 ± 421.24 | 625.15*** ± 136.23 |
| Composition 3 | 764.29** ± 197.51 | 1545.00** ± 184.64 | 1029.29** ± 295.43 | 1312.86 ± 205.78 | 787.14*** ± 276.09 |
| Composition 4 | 795.52** ± 352.16 | 1536.65** ± 245.26 | 1885.39*** ± 152.32 | 2345.36 ± 452.36 | 680.36*** ± 152.36 |
| Composition 5 | 774.46** ± 315.32 | 1556.32** ± 225.36 | 1847.37*** ± 152.35 | 2365.26 ± 442.35 | 632.65*** ± 142.52 |
| Composition 6 | 799.56** ± 125.36 | 1577.50** ± 152.52 | 1052.63** ± 275.26 | 1354.68 ± 256.62 | 756.32*** ± 275.54 |
| Composition 7 | 756.35** ± 341.25 | 1545.29** ± 241.28 | 1826.24*** 141.62 | 2345.95 ± 446.35 | 684.36*** ± 151.62 |
| Composition 8 | 778.32** ± 151.62 | 1568.25** ± 141.62 | 1814.63** ± 275.26 | 1341.62 ± 248.69 | 742.95*** ± 274.68 |
| Composition 9 | 754.65** ± 248.69 | 1566.32** ± 354.36 | 952.36** ± 225.37 | 1558.52 ± 234.58 | 735.25*** ± 252.36 |
| Composition 10 | 777.29** ± 305.26 | 2221.02*** ± 451.23 | 748.36*** ± 291.52 | 1345.62 ± 248.95 | 797.25*** ± 262.35 |
| Composition 11 | 746.43** ± 356.32 | 3056.24*** ± 612.31 | 625.36*** ± 202.64 | 1152.62 ± 325.36 | 729.31*** ± 245.69 |
| Composition 12 | 785.62** ± 355.26 | 3092.62*** ± 615.62 | 652.35*** ± 215.62 | 1162.34 ± 324.28 | 728.62*** ± 244.62 |
| Composition 13 | 762.34** ± 253.36 | 1545.62** ± 355.67 | 958.95** ± 224.68 | 1578.96 ± 235.25 | 738.68*** ± 253.64 |
| Composition 14 | 785.64** ± 315.64 | 2258.65*** ± 415.63 | 749.64*** ± 299.74 | 1349.95 ± 274.67 | 785.95*** ± 254.63 |
| Composition 15 | 795.62** ± 347.96 | 3026.92*** ± 641.65 | 656.38*** ± 215.64 | 1185.69 ± 347.67 | 748.91*** ± 246.74 |
| Composition 16 | 747.29** ± 362.35 | 3085.64*** ± 616.42 | 665.42*** ± 262.34 | 1195.68 ± 348.75 | 785.62*** ± 252.75 |
| Composition 17 | 716.24** ± 385.46 | 1516.64** ± 235.62 | 1885.95*** ± 156.24 | 2374.82 ± 452.64 | 639.75*** ± 152.61 |
| Composition 18 | 789.52** ± 162.54 | 1574.61** ± 155.26 | 1065.39** ± 285.62 | 1395.64 ± 274.68 | 774.69*** ± 211.56 |
| Composition 19 | 767.58** ± 395.62 | 1463.27** ± 249.46 | 186.95*** ± 145.61 | 2375.65 ± 445.82 | 695.61*** ± 174.26 |
| Composition 20 | 799.52** ± 152.42 | 1595.64** ± 152.61 | 1814.31** ± 276.42 | 1375.26 ± 295.61 | 767.28*** ± 279.64 |
| Composition 21 | 766.45** ± 256.24 | 1574.52** ± 336.14 | 965.29** ± 252.36 | 1596.34 ± 248.25 | 764.25*** ± 265.24 |
| Composition 22 | 722.25** ± 325.14 | 2144.62*** ± 455.45 | 786.34*** ± 274.52 | 1364.25 ± 248.36 | 788.47*** ± 225.25 |
| Composition 23 | 733.33** ± 355.66 | 3052.10*** ± 652.41 | 644.54*** ± 214.62 | 1265.84 ± 345.61 | 796.31*** ± 265.34 |
| Composition 24 | 735.35** ± 347.84 | 3045.85*** ± 645.26 | 675.64*** ± 216.42 | 1164.52 ± 326.15 | 729.57*** ± 256.24 |
| Composition 25 | 726.35** ± 246.34 | 1565.28** ± 365.28 | 948.34** ± 256.24 | 1568.17 ± 252.36 | 764.25*** ± 296.31 |
| Composition 26 | 756.47** ± 352.34 | 2262.34*** ± 485.95 | 757.25*** ± 256.24 | 1395.45 ± 257.26 | 764.25*** ± 256.24 |
| Composition 27 | 764.62** ± 346.95 | 3045.28*** ± 665.47 | 685.25*** ± 254.95 | 1147.59 ± 346.75 | 757.29*** ± 229.42 |
| Composition 28 | 742.34** ± 332.65 | 3088.95*** ± 641.25 | 695.64*** ± 234.26 | 1167.18 ± 357.96 | 786.28*** ± 279.64 |
| Composition 29 | 736.34** ± 352.95 | 3074.25*** ± 652.64 | 684.76*** ± 262.34 | 1174.95 ± 346.28 | 775.36*** ± 264.39 |
| Composition 30 | 716.37** ± 362.34 | 2156.72*** ± 464.24 | 775.62*** ± 248.29 | 1358.29 ± 229.28 | 774.29*** ± 252.41 |
| Composition 31 | 799.58** ± 356.24 | 3047.75*** ± 664.62 | 662.24*** ± 294.78 | 1246.29 ± 342.54 | 794.19*** ± 245.28 |
| Composition 32 | 785.61** ± 327.26 | 3056.31*** ± 656.31 | 648.95*** ± 256.23 | 1157.98 ± 326.34 | 775.29*** ± 248.27 |
| Composition 33 | 765.26** ± 245.68 | 1575.94** ± 346.29 | 956.28*** ± 246.27 | 1574.18 ± 265.24 | 746.29*** ± 274.82 |
| Composition 34 | 777.18** ± 342.15 | 2275.29*** ± 426.34 | 726.34*** ± 247.29 | 1374.29 ± 248.96 | 774.82*** ± 252.34 |
| Composition 35 | 767.29** ± 352.61 | 3074.16*** ± 626.85 | 664.15*** ± 226.59 | 1176.29 ± 356.34 | 769.25*** ± 266.92 |
| Composition 36 | 783.36** ± 329.37 | 3071.25*** ± 662.35 | 649.62*** ± 236.31 | 1178.96 ± 348.72 | 764.25*** ± 216.26 |

TABLE 9-continued

Result of PAF content ($\bar{x}$ ± SD, ng/L)

| Group | 0.5 h after administration | 1 h after administration | 2 h after administration | 3 h after administration | 4 h after administration |
| --- | --- | --- | --- | --- | --- |
| Composition 37 | 795.62** ± 334.26 | 3045.62*** ± 674.29 | 634.59*** ± 249.25 | 1148.95 ± 326.72 | 764.25*** ± 253.92 |
| Composition 38 | 720.35** ± 351.75 | 2264.28*** ± 462.35 | 741.26*** ± 262.53 | 1348.96 ± 226.24 | 756.29*** ± 248.26 |
| Composition 39 | 732.62** ± 315.64 | 3085.64*** ± 615.52 | 686.42*** ± 274.46 | 1186.29 ± 341.72 | 749.75*** ± 246.29 |
| Composition 40 | 740.29** ± 352.67 | 3029.54*** ± 675.29 | 646.28*** ± 245.28 | 1148.57 ± 385.25 | 795.25*** ± 246.28 |
| Composition 41 | 746.36** ± 346.52 | 3075.69*** ± 664.28 | 686.27*** ± 256.29 | 1175.26 ± 347.64 | 787.16*** ± 248.28 |

1) Model group vs control group $p > 0.05$,
2) Model group vs drug group. *$p < 0.05$, $p < 0.01$ *$p < 0.001$ From table 9: 1) 0.5 h-4 h after administration, comparing the PAF (Platelet activating factor) content of model group with the control group, no obviously difference was observed ($p>0.05$), indicating the success of the modeling. 2) Compared to model group, 2 h after administration, the PAF content of the Ginkgolide B group decreased significantly ($p<0.01$), and 4 h after administration, the PAF content of the Rivaroxaban and Apixaban groups had extremely significant decrease ($p<0.001$), the PAF content of the Razaxaban and Otamixaban decreased significantly ($p<0.01$), 3) Compared to model group, 0.5 h after administration, the PAF content of all the compositions groups decreased significantly ($p<0.01$), indicating the pharmaceutical composition of the present invention can effectively decrease the PAF content and the Ginkgolide B and xaban work synergistically on the blocking of PAF receptor. 1 h after administration, the PAF content of the composition groups had extremely significant decrease ($p<0.001$) and significant decrease ($p<0.01$), indicating the Ginkgolide B and Apixaban work synergistically on the blocking of PAF receptor. 2 h after administration, the PAF content of the composition groups had extremely significant decrease ($p<0.001$) and significant decrease ($p<0.01$), indicating the Ginkgolide B and Apixaban work synergistically on the blocking of PAF receptor.

From table 6 to table 9, one can see that:

Among the compositions comprising Ginkgolide B and Rivaroxaban (Composition 1-8), the aPPT of composition 1, 5-8 is relatively longer, PT of the same compositions is longer, the anti-factor Xa activity of the same compositions is higher, the PAF content of the same compositions is lower and the aPPT of composition 1 is the longest, PT of composition 1 is the longest, the anti-factor Xa activity of composition 1 is the highest, the PAF content of composition 1 is the lowest. Therefore, among the compositions comparing Ginkgolide B and Rivaroxaban, preferably, Ginkgolide B is in an amount of 5-15 parts by weight and Rivaroxaban is in an amount of 10-20 by weight; most preferably, Ginkgolide B is in an amount of 10 parts by weight and Rivaroxaban is in an amount of 15 parts by weight.

Among the compositions comprising Ginkgolide B and Apixaban (Composition 9-16), the aPPT of composition 9, 13-16 is relatively longer, PT of the same compositions is longer, the anti-factor Xa activity of the same compositions is higher, the PAF content of the same compositions is lower and the aPPT of composition 9 is the longest, PT of composition 9 is the longest, the anti-factor Xa activity of composition 9 is the highest, and the PAF content of composition 9 is the lowest. Therefore, among the compositions comprising Ginkgolide B and Apixaban, preferably, Ginkgolide B is in an amount of 5-15 parts by weight and Apixaban is in an amount of 1-10 by weight; most preferably, Ginkgolide B is in an amount of 10 parts by weight and Apixaban is in an amount of 5 parts by weight.

Among the compositions comprising Ginkgolide B and Edoxaban (Composition 17-24), the aPPT of composition 17, 22-24 is relatively longer, PT of the same compositions is longer, the anti-factor Xa activity of the same compositions is higher, the PAF content of the same compositions is lower and the aPPT of composition 17 is the longest, PT of composition 17 is the longest, the anti-factor Xa activity of composition 17 is the highest, the PAF content of composition 17 is the lowest. Therefore, among the compositions comprising Ginkgolide B and Edoxaban, preferably, Ginkgolide B is in an amount of 5-15 parts by weight and Edoxaban is in an amount of 10-30 by weight; most preferably, Ginkgolide B is in an amount of 10 parts by weight and Edoxaban is in an amount of 15 parts by weight.

Among the compositions comprising Ginkgolide B and Razaxaban (Composition 25-29), the aPPT of composition 25, 28-29 is relatively longer, PT of the same compositions is longer, the anti-factor Xa activity of the same compositions is higher, the PAF content of the same compositions is lower and the aPPT of composition 25 is the longest, PT of composition 25 is the longest, the anti-factor Xa activity of composition 25 is the highest, the PAF content of composition 25 is the lowest. Therefore, among the compositions comprising Ginkgolide B and Razaxaban, preferably, Ginkgolide B is in an amount of 5-15 parts by weight and Razaxaban is in an amount of 5-15 by weight; most preferably, Ginkgolide B is in an amount of 10 parts by weight and Razaxaban is in an amount of 10 parts by weight.

Among the compositions comprising Ginkgolide B and Otamixaban (Composition 30-41), the aPPT of composition 30, 38-41 is relatively longer, PT of the same compositions is longer, the anti-factor Xa activity of the same compositions is higher, the PAF content of the same compositions is lower and the aPPT of composition 30 is the longest, PT of composition 30 is the longest, the anti-factor Xa activity of composition 30 is the highest, the PAF content of composition 30 is the lowest. Therefore, among the compositions comprising Ginkgolide B and Otamixaban, preferably, Ginkgolide B is in an amount of 8-12 parts by weight and Otamixaban is in an amount of 50-90 parts by weight; most preferably, Ginkgolide B is in an amount of 10 parts by weight and Otamixaban is in an amount of 10 parts by weight.

The experimental results showed that the combination use of Ginkgolide B and xaban type drug like Rivaroxaban, Apixaban, Edoxaban, Razaxaban or Otamixaban as active ingredients can remarkably prolong aPPT and PT, increase the anti-factor Xa activity and lower the PAF content. Combined usage of Ginkgolide B and xaban drug results a synergistic effect and is better than using Ginkgolide B or xaban drug alone. Combined usage of Ginkgolide B and xaban drug functions through different mechanisms and results a long aPPT and PT, increased anti-factor Xa activity and low PAF content.

In conclusion, the combination use of Ginkgolide B and xaban type drug of the present invention work synergistically and can effectively inhibit the aggregation of platelet. The use of the pharmaceutical combination in clinic is quite promising.

The invention claimed is:

1. A pharmaceutical composition comprising:
   Ginkgolide B in an amount of 1-20 parts by weight, and
   Rivaroxaban in an amount of 5-40 parts by weight.

2. A method for preparing the pharmaceutical composition of claim 1, comprising the following steps:
   S1: weighing out raw materials of Ginkgolide B and Rivaroxaban according to the parts by weight of claim 1; and
   S2: mixing the raw materials, and adding a pharmaceutically acceptable auxiliary to the raw materials to prepare a common pharmaceutical preparation.

3. A method for anti-platelet aggregation, comprising administering the pharmaceutical composition of claim 1 to a subject in need thereof.

4. The pharmaceutical composition of claim 1, wherein Ginkgolide B is in an amount of 5-15 parts by weight and Rivaroxaban is in an amount of 10-20 parts by weight.

5. The pharmaceutical composition of claim 4, wherein Ginkgolide B is in an amount of 10 parts by weight and Rivaroxaban is in an amount of 15 parts by weight.

6. The method of claim 3, wherein Ginkgolide B is in an amount of 10 parts by weight and Rivaroxaban is in an amount of 15 parts by weight.

* * * * *